(12) United States Patent
Somlo et al.

(10) Patent No.: US 6,228,591 B1
(45) Date of Patent: May 8, 2001

(54) POLYCYSTIC KIDNEY DISEASE PKD2 GENE AND USES THEREOF

(75) Inventors: Stefan Somlo, Westport, CT (US); Toshio Mochizuki, Tokyo (JP)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/385,752

(22) Filed: Aug. 30, 1999

Related U.S. Application Data

(63) Continuation of application No. 08/651,999, filed on May 23, 1996, now Pat. No. 6,031,088.

(51) Int. Cl.$^7$ ........................................................ C12Q 1/68
(52) U.S. Cl. ............................................................... 435/6
(58) Field of Search ............................ 435/6, 7.1; 436/94

(56) References Cited

PUBLICATIONS

San Millan et al. Am. J. Hum. Genet. 56:248–253, Jan. 1995.*

* cited by examiner

*Primary Examiner*—Karen Cochrane Carlson
*Assistant Examiner*—Devesh Srivastava
(74) *Attorney, Agent, or Firm*—Amster, Rothstein & Ebenstein

(57) ABSTRACT

The present invention provides a purified and isolated wild type PKD2 gene, as well as mutated forms of this gene. The present invention also provides one or more single-stranded nucleic acid probes which specifically hybridize to the wild type PKD2 gene or the mutated PKD2 gene, and mixtures thereof, which may be formulated in kits, and used in the diagnosis of ADPKD associated with the mutated PKD2 gene. The present invention also provides a method for diagnosing ADPKD caused by a mutated PKD2 gene, as well as a method for treating autosomal dominant polycystic kidney disease caused by a mutated PKD2 gene.

3 Claims, 12 Drawing Sheets

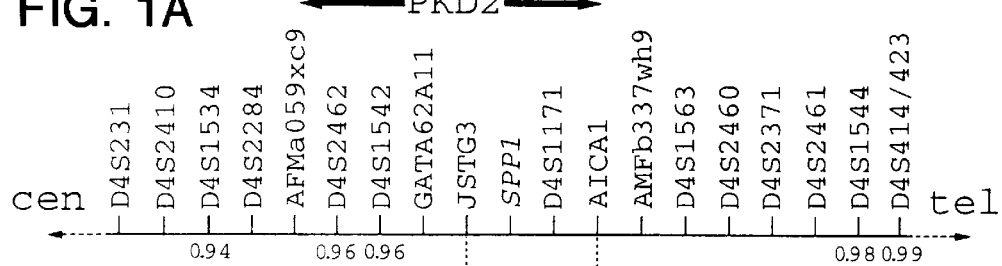
FIG. 1A
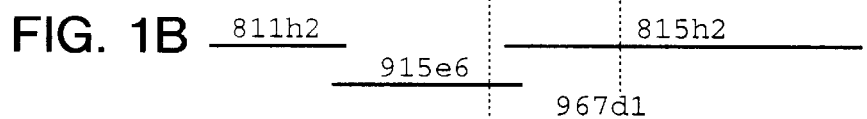
FIG. 1B
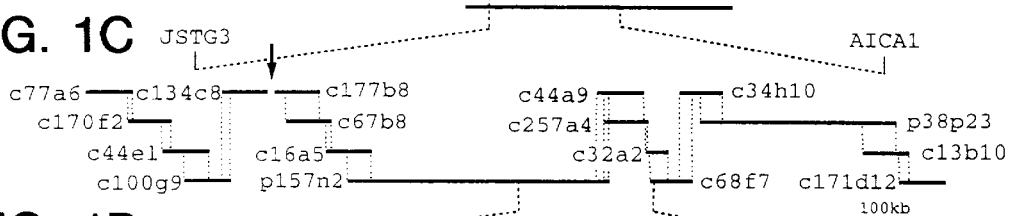
FIG. 1C
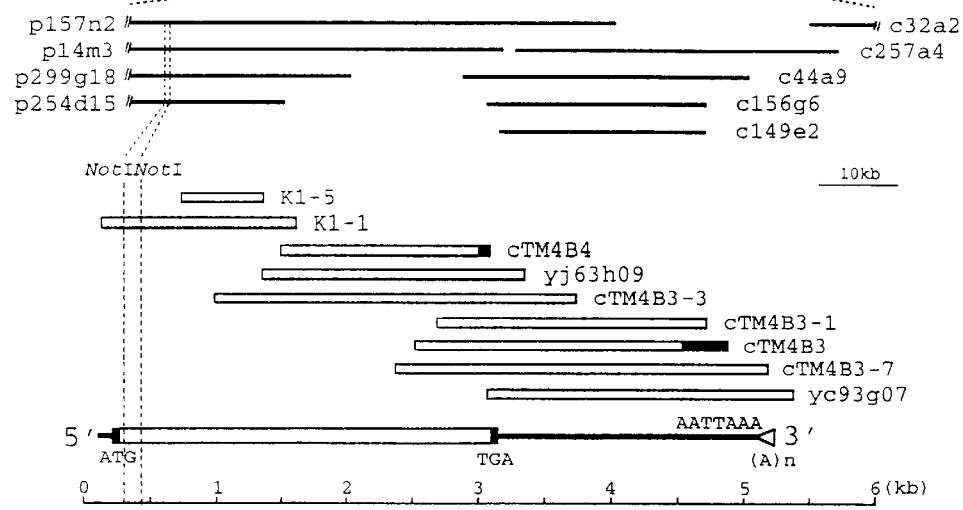
FIG. 1D
FIG. 1E

Family 97

Family 1605

Family 1601

```
cTM-4    MVNSSRVQPQOPGDAKRPPAPRAPDPGRLMAGCAAVGASLAAPGGLCEQRGLEIEMQRIRQAAARDPPAGAAASPSPPLSSCSRQAWSRDNPGFEAEEEE   100 cTM-4    EEVEGEEGMVVEMDVEWRPGSRRSAASSAVSSVGARSRGLGGYHGAGHPSGRRRREDQGPPCPSPVGGGDPLHRHLPLEGQPPRVAWAERLVRGLRGL        200
                                                              *
cTM-4    WGTRLMEESSTNREKYLKSVLRELVTYLLLFLIVLCILTYGMMSSNVYYTRMSQLFLDTPVSKTEKTNFKTLSSMEDFWKFTEGSLLDGLYWKMQPSNQ       300
             ::::|||:|:|:|:|:||::||:|::|::|||::::::::::|::|:::|:|||
PKD1 (3655)FLAKEEARKVKRLHGMLRSLLVMLFLLVTLLASYGDASCHGAY.RLQS......AIKQELHSRAFLAITRSEELWPWMAHVLLPYVH.....GNQ
ZK945.9  (1708)ENRKMRDEQLFITIRDMLCFFASLYIMVMLTYCKDRHGYWYQLEMSTILNINQKNYGDNT.FMSIQHADDFWDWARESLATALLASWYDGNP
                                                       *                                              97
cTM-4    TEADNRSFIFYENLLLGVPRIRQLRVRNGSCSIPQDLRDEIKECYDVYSVSSEDRAPFGPRNGTA.WIY.TSEKDLNGSSHWGIIATYSGAGYYLDLSRTRE    400
              ::|:    :||:|::|::::       ||||||||:|:||||:|||:|
PKD1     SSPE......LGPPRLRQVRLQEALYPDPPGPRVHTCSAAGGFSTSDYDVGWESPHNGSGTWAY..:SAPDLLGAWSWGSCAVYDSSGYVQELGLSLE
ZK945.9  AYGMRAYMNDKVSRSMGIGTIRQVRTKS       (1878)YTYKTSE.ELSTETVSGLLYSYSGGGYTISMSGTQA
                1601                                                     tm2
cTM-4    ETAAQVASLKKNVWLDRGTRATFIDFSVYNANINLFCVVRLLVEFPATGGVIPSWQFQPLKLIRYVTTFDFFLAACEIIFCFFIFYVVEEILE.IRIHKL    500
              ::|:|:|||:|:::::|:::::||:::::::|:|:|:|::::::::|:||::::|::::|:::|:|:|:||:||:|:::||::|||::||: |::
PKD1     ESRDRLRFLQLIHNWLDNRSRAVFLELITRYSPAVGLHAAVTLRLEFPAAGRALAALSVRPFALRRLSAGLSLPLLTSVCLLLFAVHFAVAEAARTW.HREGRW
ZK945.9  EIITLFNKLDSERWIDDHTRAVIIEFSAYNAQINYFSVVQLLVEIPKSGIYLPNSWVESVRLIKSEGSDGTVVKYYEMLYIFFSVLIFVKEIV    (2005)
                                                                                 (1517)FTMVFSLECVLKVIAFGFL
VACC α1E-1                                                                                        tm4
                                                                                           *
cTM-4    HYFR.SFWNCLDVIVVLSVVAIGINIYRTSNVEV.LLQFL.EDQNTFPNFEEHLAYWQIQFNNIAAVTVFFVWIKLFKFINFNRTMSQLSTTMSRCAKDLF  598
         ||:| |  | ::|::||:| |:|:: ||:: |:|::||:: ||::|:|||:|||:|:  |::|:|:|:|||:|| || |:|:
PKD1     RVLRLGAWARWLLVALTAATALVRLAQLGAADRQ..WTRFVRGRPRFTSFDQVAQLSSAARGLAASLLFLLLVKAAQOLRFVRQWSVFGKTLCRALPELL
ZK945.9              (2039)WNFMDLIVGALAVASVLAYTIRQRTTNRAMEDFNANNGNSYINLTEQRNWEIVFSYCLAGAVFFTSCKMIRILRFNRIGVLAATLDNALGAIV
VACC α1E-1   NYFR.DTWNIFDFITVIGSITEIILTDSKLVNTSG.F.......NMSFLK.......             LFRAARLIKLLRQGYTIRILLWTFVQSFKALP
                                                                                                      tm6
         tm5                                                                              *
cTM-4    GFAIMFFIIFLAYAQLAYLVFGTQVDDFSTFQECIFTQFRIILGDINFAEIEEAN.RVLGPIYFTTFVFMFFILLNMFLAIINDTYSEVKSDL...AQQKA  696
         |:::||::|:|||:|:|:|:  ::::::|::|:::::|::|::|:::::::|:|| :::|||:|||||:||||:|:|:|||| |:::|::::   |:::
PKD1     GVTLGLVVLGVAYAQLAILLVSSCVVDSIWSVAQAII..........VLCPGTGLSLCPAESWHLSPLLCVGIWALRLWGALRLGAVILRWRYHALRGELYRPAWEPQ
ZK945.9  SFGIAFLFFSMTFNSVLYAVLGNKMGGYRSLMATFQTALAGMLGKLDVTSIQP.....ISQFAFVVIMLYMI(2199)
VACC α1E-1       YVCLLIAMLFFIYAIIGMQVFG     NFFRSFFGSLMLLFRSATGE.AWQEIERCG.TDIAYVYFVSFIFFCSFLMLNLFVAVIMDNFEYLTRD.......
                          (1630)    (1644)                   (1668)    (1692)
                                                                     1605
cTM-4    EMELSDLIRKGYHKALVKLIKKNTVDDISESLRQGGKILNFDELRQDLKGKGHTDAEIEAIFTKYDQDGDQELTEHEHQQMRDDLEKEREDLDHSSLPR   800
         ::::::|||:|     ::|:|||
PKD1     DYEMVELF......LRRLRL (4139)
ZK945.9
VACC α1E-1
                                                (2216) EFEEIRNDSEKQTNDYEI (2233)
cTM-4    PMSRSFPRSLDDSEEDDDEDSGHSSRRRGSISSGVSYEEFQVLVRRVDRMEHSIGSIVSKIDAVIVKLEIMERAKLKRREVLGRLLDGVAEDERLGRDSEI  900
                                                      |:| ||:||  :| ||||  |:|:::| |::|
cTM-4    HREQMERLIVREELERWESDDAASQISHGLGTPVGLNGQPRPRSSRPSSSQS.TEGMEGAGNGSSNVHV   968
            |||::|      ||::|:|||||:|||||::||  :: |||| |  :|    ||::||
VACC α1E-1 (2039)ERRRSKERKHLLSPDVSRCNSEERGTQADWESPERRQSRSPSEGRSQIPNRQGTGSLSESSI (2100)
```

FIG. 4A

```
EIEAIFTKYDQDGDQELTEHEHQQMRDDL  (754-782)
 — —   — — * * * — : — — — — —
 n n   n * Y Z G I E n n n       (EF-hand test)
       X Y Z -Y -X -Z
       (coordination vertices)
```

FIG. 4B

```
                                        GGC TCC TGA GGC GCA CAG      18

CGC CGA GCG CGG CGC CGC GCA CCC GCG CGC CGG ACG CCA GTG ACC GCG      66

ATG GTG AAC TCC AGT CGC GTG CAG CCT CAG CAG CCC GGG GAC GCC AAG     114
Met Val Asn Ser Ser Arg Val Gln Pro Gln Gln Pro Gly Asp Ala Lys
 1            5                      10                      15

CGG CCG CCC GCG CCC CGC GCG CCG GAC CCG GGC CGG CTG ATG GCT GGC     162
Arg Pro Pro Ala Pro Arg Ala Pro Asp Pro Gly Arg Leu Met Ala Gly
                20                      25                      30

TGC GCG GCC GTG GGC GCC AGC CTC GCC GCC CCG GGC GGC CTC TGC GAG     210
Cys Ala Ala Val Gly Ala Ser Leu Ala Ala Pro Gly Gly Leu Cys Glu
            35                      40                      45

CAG CGG GGC CTG GAG ATC GAG ATG CAG CGC ATC CGG CAG GCG GCC GCG     258
Gln Arg Gly Leu Glu Ile Glu Met Gln Arg Ile Arg Gln Ala Ala Ala
        50                      55                      60

CGG GAC CCC CCG GCC GGA GCC GCG GCC TCC CCT TCT CCT CCG CTC TCG     306
Arg Asp Pro Pro Ala Gly Ala Ala Ala Ser Pro Ser Pro Pro Leu Ser
65                      70                      75                  80

TCG TGC TCC CGG CAG GCG TGG AGC CGC GAT AAC CCC GGC TTC GAG GCC     354
Ser Cys Ser Arg Gln Ala Trp Ser Arg Asp Asn Pro Gly Phe Glu Ala
                85                      90                      95

GAG GAG GAG GAG GAG GAG GTG GAA GGG GAA GAA GGC GGA ATG GTG GTG     402
Glu Glu Glu Glu Glu Glu Val Glu Gly Glu Glu Gly Gly Met Val Val
                100                     105                     110

GAG ATG GAC GTA GAG TGG CGC CCG GGC AGC CGG AGG TCG GCC GCC TCC     450
Glu Met Asp Val Glu Trp Arg Pro Gly Ser Arg Arg Ser Ala Ala Ser
            115                     120                     125

TCG GCC GTG AGC TCC GTG GGC GCG CGG AGC CGG GGG CTT GGG GGC TAC     498
Ser Ala Val Ser Ser Val Gly Ala Arg Ser Arg Gly Leu Gly Gly Tyr
        130                     135                     140

CAC GGC GCG GGC CAC CCG AGC GGG AGG CGG CGC CGG CGA GAG GAC CAG     546
His Gly Ala Gly His Pro Ser Gly Arg Arg Arg Arg Glu Asp Gln
145                     150                     155                 160

GGC CCG CCG TGC CCC AGC CCA GTC GGC GGC GGG GAC CCG CTG CAT CGC     594
Gly Pro Pro Cys Pro Ser Pro Val Gly Gly Gly Asp Pro Leu His Arg
                165                     170                     175

CAC CTC CCC CTG GAA GGG CAG CCG CCC CGA GTG GCC TGG GCG GAG AGG     642
His Leu Pro Leu Glu Gly Gln Pro Pro Arg Val Ala Trp Ala Glu Arg
                180                     185                     190
```

FIG. 5A

```
CTG GTT CGC GGG CTG CGA GGT CTC TGG GGA ACA AGA CTC ATG GAG GAA    690
Leu Val Arg Gly Leu Arg Gly Leu Trp Gly Thr Arg Leu Met Glu Glu
        195                 200                 205

AGC AGC ACT AAC CGA GAG AAA TAC CTT AAA AGT GTT TTA CGG GAA CTG    738
Ser Ser Thr Asn Arg Glu Lys Tyr Leu Lys Ser Val Leu Arg Glu Leu
        210                 215                 220

GTC ACA TAC CTC CTT TTT CTC ATA GTC TTG TGC ATC TTG ACC TAC GGC    786
Val Thr Tyr Leu Leu Phe Leu Ile Val Leu Cys Ile Leu Thr Tyr Gly
225                 230                 235                 240

ATG ATG AGC TCC AAT GTG TAC TAC TAC ACC CGG ATG ATG TCA CAG CTC    834
Met Met Ser Ser Asn Val Tyr Tyr Tyr Thr Arg Met Met Ser Gln Leu
                245                 250                 255

TTC CTA GAC ACC CCC GTG TCC AAA ACG GAG AAA ACT AAC TTT AAA ACT    882
Phe Leu Asp Thr Pro Val Ser Lys Thr Glu Lys Thr Asn Phe Lys Thr
            260                 265                 270

CTG TCT TCC ATG GAA GAC TTC TGG AAG TTC ACA GAA GGC TCC TTA TTG    930
Leu Ser Ser Met Glu Asp Phe Trp Lys Phe Thr Glu Gly Ser Leu Leu
        275                 280                 285

GAT GGG CTG TAC TGG AAG ATG CAG CCC AGC AAC CAG ACT GAA GCT GAC    978
Asp Gly Leu Tyr Trp Lys Met Gln Pro Ser Asn Gln Thr Glu Ala Asp
290                 295                 300

AAC CGA AGT TTC ATC TTC TAT GAG AAC CTG CTG TTA GGG GTT CCA CGA   1026
Asn Arg Ser Phe Ile Phe Tyr Glu Asn Leu Leu Leu Gly Val Pro Arg
305                 310                 315                 320

ATA CGG CAA CTC CGA GTC AGA AAT GGA TCC TGC TCT ATC CCC CAG GAC   1074
Ile Arg Gln Leu Arg Val Arg Asn Gly Ser Cys Ser Ile Pro Gln Asp
            325                 330                 335

TTG AGA GAT GAA ATT AAA GAG TGC TAT GAT GTC TAC TCT GTC AGT AGT   1122
Leu Arg Asp Glu Ile Lys Glu Cys Tyr Asp Val Tyr Ser Val Ser Ser
        340                 345                 350

GAA GAT AGG GCT CCC TTT GGG CCC CGA AAT GGA ACC GCT TGG ATC TAC   1170
Glu Asp Arg Ala Pro Phe Gly Pro Arg Asn Gly Thr Ala Trp Ile Tyr
        355                 360                 365

ACA AGT GAA AAA GAC TTG AAT GGT AGT AGC CAC TGG GGA ATC ATT GCA   1218
Thr Ser Glu Lys Asp Leu Asn Gly Ser Ser His Trp Gly Ile Ile Ala
        370                 375                 380

ACT TAT AGT GGA GCT GGC TAT TAT CTG GAT TTG TCA AGA ACA AGA GAG   1266
Thr Tyr Ser Gly Ala Gly Tyr Tyr Leu Asp Leu Ser Arg Thr Arg Glu
385                 390                 395                 400
```

FIG. 5B

```
GAA ACA GCT GCA CAA GTT GCT AGC CTC AAG AAA AAT GTC TGG CTG GAC   1314
Glu Thr Ala Ala Gln Val Ala Ser Leu Lys Lys Asn Val Trp Leu Asp
            405                 410                 415

CGA GGA ACC AGG GCA ACT TTT ATT GAC TTC TCA GTG TAC AAC GCC AAC   1362
Arg Gly Thr Arg Ala Thr Phe Ile Asp Phe Ser Val Tyr Asn Ala Asn
            420                 425                 430

ATT AAC CTG TTC TGT GTG GTC AGG TTA TTG GTT GAA TTC CCA GCA ACA   1410
Ile Asn Leu Phe Cys Val Val Arg Leu Leu Val Glu Phe Pro Ala Thr
            435                 440                 445

GGT GGT GTG ATT CCA TCT TGG CAA TTT CAG CCT TTA AAG CTG ATC CGA   1458
Gly Gly Val Ile Pro Ser Trp Gln Phe Gln Pro Leu Lys Leu Ile Arg
            450                 455                 460

TAT GTC ACA ACT TTT GAT TTC TTC CTG GCA GCC TGT GAG ATT ATC TTT   1506
Tyr Val Thr Thr Phe Asp Phe Phe Leu Ala Ala Cys Glu Ile Ile Phe
465                 470                 475                 480

TGT TTC TTT ATC TTT TAC TAT GTG GTG GAA GAG ATA TTG GAA ATT CGC   1554
Cys Phe Phe Ile Phe Tyr Tyr Val Val Glu Glu Ile Leu Glu Ile Arg
            485                 490                 495

ATT CAC AAA CTA CAC TAT TTC AGG AGT TTC TGG AAT TGT CTG GAT GTT   1602
Ile His Lys Leu His Tyr Phe Arg Ser Phe Trp Asn Cys Leu Asp Val
            500                 505                 510

GTG ATC GTT GTG CTG TCA GTG GTA GCT ATA GGA ATT AAC ATA TAC AGA   1650
Val Ile Val Val Leu Ser Val Val Ala Ile Gly Ile Asn Ile Tyr Arg
            515                 520                 525

ACA TCA AAT GTG GAG GTG CTA CTA CAG TTT CTG GAA GAT CAA AAT ACT   1698
Thr Ser Asn Val Glu Val Leu Leu Gln Phe Leu Glu Asp Gln Asn Thr
530                 535                 540

TTC CCC AAC TTT GAG CAT CTG GCA TAT TGG CAG ATA CAG TTC AAC AAT   1746
Phe Pro Asn Phe Glu His Leu Ala Tyr Trp Gln Ile Gln Phe Asn Asn
545                 550                 555                 560

ATA GCT GCT GTC ACA GTA TTT TTT GTC TGG ATT AAG CTC TTC AAA TTC   1794
Ile Ala Ala Val Thr Val Phe Phe Val Trp Ile Lys Leu Phe Lys Phe
            565                 570                 575

ATC AAT TTT AAC AGG ACC ATG AGC CAG CTC TCG ACA ACC ATG TCT CGA   1842
Ile Asn Phe Asn Arg Thr Met Ser Gln Leu Ser Thr Thr Met Ser Arg
            580                 585                 590

TGT GCC AAA GAC CTG TTT GGC TTT GCT ATT ATG TTC TTC ATT ATT TTC   1890
Cys Ala Lys Asp Leu Phe Gly Phe Ala Ile Met Phe Phe Ile Ile Phe
            595                 600                 605
```

FIG. 5C

```
CTA GCG TAT GCT CAG TTG GCA TAC CTT GTC TTT GGC ACT CAG GTC GAT    1938
Leu Ala Tyr Ala Gln Leu Ala Tyr Leu Val Phe Gly Thr Gln Val Asp
    610             615                 620

GAC TTC AGT ACT TTC CAA GAG TGT ATC TTC ACT CAA TTC CGT ATC ATT    1986
Asp Phe Ser Thr Phe Gln Glu Cys Ile Phe Thr Gln Phe Arg Ile Ile
625                 630                 635                 640

TTG GGC GAT ATC AAC TTT GCA GAG ATT GAG GAA GCT AAT CGA GTT TTG    2034
Leu Gly Asp Ile Asn Phe Ala Glu Ile Glu Glu Ala Asn Arg Val Leu
                645                 650                 655

GGA CCA ATT TAT TTC ACT ACA TTT GTG TTC TTT ATG TTC TTC ATT CTT    2082
Gly Pro Ile Tyr Phe Thr Thr Phe Val Phe Phe Met Phe Phe Ile Leu
            660                 665                 670

TTG AAT ATG TTT TTG GCT ATC ATC AAT GAT ACT TAC TCT GAA GTG AAA    2130
Leu Asn Met Phe Leu Ala Ile Ile Asn Asp Thr Tyr Ser Glu Val Lys
        675                 680                 685

TCT GAC TTG GCA CAG CAG AAA GCT GAA ATG GAA CTC TCA GAT CTT ATC    2178
Ser Asp Leu Ala Gln Gln Lys Ala Glu Met Glu Leu Ser Asp Leu Ile
    690                 695                 700

AGA AAG GGC TAC CAT AAA GCT TTG GTC AAA CTA AAA CTG AAA AAA AAT    2226
Arg Lys Gly Tyr His Lys Ala Leu Val Lys Leu Lys Leu Lys Lys Asn
705                 710                 715                 720

ACC GTG GAT GAC ATT TCA GAG AGT CTG CGG CAA GGA GGA GGC AAG TTA    2274
Thr Val Asp Asp Ile Ser Glu Ser Leu Arg Gln Gly Gly Gly Lys Leu
                725                 730                 735

AAC TTT GAC GAA CTT CGA CAA GAT CTC AAA GGG AAG GGC CAT ACT GAT    2322
Asn Phe Asp Glu Leu Arg Gln Asp Leu Lys Gly Lys Gly His Thr Asp
            740                 745                 750

GCA GAG ATT GAG GCA ATA TTC ACA AAG TAC GAC CAA GAT GGA GAC CAA    2370
Ala Glu Ile Glu Ala Ile Phe Thr Lys Tyr Asp Gln Asp Gly Asp Gln
        755                 760                 765

GAA CTG ACC GAA CAT GAA CAT CAG CAG ATG AGA GAC GAC TTG GAG AAA    2418
Glu Leu Thr Glu His Glu His Gln Gln Met Arg Asp Asp Leu Glu Lys
    770                 775                 780

GAG AGG GAG GAC CTG GAT TTG GAT CAC AGT TCT TTA CCA CGT CCC ATG    2466
Glu Arg Glu Asp Leu Asp Leu Asp His Ser Ser Leu Pro Arg Pro Met
785                 790                 795                 800

AGC AGC CGA AGT TTC CCT CGA AGC CTG GAT GAC TCT GAG GAG GAT GAC    2514
Ser Ser Arg Ser Phe Pro Arg Ser Leu Asp Asp Ser Glu Glu Asp Asp
                805                 810                 815
```

FIG. 5D

```
GAT GAA GAT AGC GGA CAT AGC TCC AGA AGG AGG GGA AGC ATT TCT AGT   2562
Asp Glu Asp Ser Gly His Ser Ser Arg Arg Arg Gly Ser Ile Ser Ser
            820             825                 830

GGC GTT TCT TAC GAA GAG TTT CAA GTC CTG GTG AGA CGA GTG GAC CGG   2610
Gly Val Ser Tyr Glu Glu Phe Gln Val Leu Val Arg Arg Val Asp Arg
            835             840                 845

ATG GAG CAT TCC ATC GGC AGC ATA GTG TCC AAG ATT GAC GCC GTG ATC   2658
Met Glu His Ser Ile Gly Ser Ile Val Ser Lys Ile Asp Ala Val Ile
        850                 855                 860

GTG AAG CTA GAG ATT ATG GAG CGA GCC AAA CTG AAG AGG AGG GAG GTG   2706
Val Lys Leu Glu Ile Met Glu Arg Ala Lys Leu Lys Arg Arg Glu Val
865                 870                 875                 880

CTG GGA AGG CTG TTG GAT GGG GTG GCC GAG GAT GAA AGG CTG GGT CGT   2754
Leu Gly Arg Leu Leu Asp Gly Val Ala Glu Asp Glu Arg Leu Gly Arg
                885                 890                 895

GAC AGT GAA ATC CAT AGG GAA CAG ATG GAA CGG CTA GTA CGT GAA GAG   2802
Asp Ser Glu Ile His Arg Glu Gln Met Glu Arg Leu Val Arg Glu Glu
            900                 905                 910

TTG GAA CGC TGG GAA TCC GAT GAT GCA GCT TCC CAG ATC AGT CAT GGT   2850
Leu Glu Arg Trp Glu Ser Asp Asp Ala Ala Ser Gln Ile Ser His Gly
            915                 920                 925

TTA GGC ACG CCA GTG GGA CTA AAT GGT CAA CCT CGC CCC AGA AGC TCC   2898
Leu Gly Thr Pro Val Gly Leu Asn Gly Gln Pro Arg Pro Arg Ser Ser
        930                 935                 940

CGC CCA TCT TCC TCC CAA TCT ACA GAA GGC ATG GAA GGT GCA GGT GGA   2946
Arg Pro Ser Ser Ser Gln Ser Thr Glu Gly Met Glu Gly Ala Gly Gly
945                 950                 955                 960

AAT GGG AGT TCT AAT GTC CAC GTA TGA TAT GTG TGT TTC AGT ATG TGT   2994
Asn Gly Ser Ser Asn Val His Val
                965

GTT TCT AAT AAG TGA GGA AGT GGC TGT CCT GAA TTG CTG TAA CAA GCA   3042

CAC TAT TTA TAT GCC CTG ACC ACC ATA GGA TGC TAG TCT TTG TGA CCG   3090

ATT GCT AAT CTT CTG CAC TTT AAT TTA TTT TAT ATA AAC TTT ACC CAT   3138

GGT TCA AAG ATT TTT TTT TCT TTT TCT CAT ATA AGA AAT CTA GGT GTA   3186

AAT ATT GAG TAC AGA AAA AAA ATC TTC ATG ATG TGT ATT GAG CGG TAC   3234

GCC CAG TTG CCA CCA TGA CTG AGT CTT CTC AGT TGA CAA TGA AGT AGC   3282
```

FIG. 5E

```
CTT TTA AAG CTA GAA AAC TGT CAA AGG GCT TCT GAG TTT CAT TTC CAG   3330
TCA CAA AAA TCA GTA TTG TTA TTT TTT TCC AAG AGT GTG AAG GAA AAT   3378
GGG GCA ATT CCT TTC CAC TCT GGC ATA GTT CAT GAG CTT AAT ACA TAG   3426
CTT TCT TTT AAG AAA GGA GCC TTT TTT TTC AAC TAG CTT CCT GGG GTA   3474
AAC TTT TCT AAA AGA TAA AAT GGG AAG GAA CTC CAA ACT ATG ATA GAA   3522
TCT GTG TGA ATG GTT AAG ATG AAT GTT AAA TAC TAT GCT TTT TTG TAA   3570
GTT GAT CGT ATC TGA TGT CTG TGG GAC TAA CTG TAT CAC TTA ATT TTT   3618
ACC TTA TTT TGG CTC TAA TTT GAA TAA GCT GAG TAA AAC CAC CAA AGA   3666
TCA GTT ATA GGA TAA AAT GGC ATC TCT AAC CAT AAC ACA GGA GAA TTG   3714
GAA GGA GCC CTA AGT TGT CAC TCA GTT TAA TTT CTT TTA ATG GTT AGT   3762
TTA GCC TAA AGA TTT ATC TGC ATA TTC TTT TTC CCA TGT GGC TCT ACT   3810
CAT TTG CAA CTG AAT TTA ATG TTA TAA CTC ATC TAG TGA GAC CAA CTT   3858
ACT AAA TTT TTA GTA TGC ACT GAA AGT TTT TAT CCA ACA ATT ATG TTC   3906
ATT TTA AGC AAA ATT TTA AGA AAG TTT TGA AAT TCA TAA AGC ATT TGG   3954
TTT TAA ACT ATT TTA AGA ATA TAG TAC TCG GTC AGG TAT GNN NCA CGC   4002
CTG TAA TCC CAG CAC TTT GGG AGG CCG AAA CAG GCG AAT CAC TTG AGC   4050
CCA GGA GTT CAA GAC CAA CAT GGG CAA TGT GGC GAA ACT CCA TCT CTA   4098
CAA AAA ATG CAA AAA TAA AAA ATA TAG TAC TCA AGT ATT CTT GAT CCT   4146
GTG TTT CAA AAC TAG AAT TTG TAA TGC AAA TGG AGC TCA GTC TAA TAA   4194
AAA AGA GGT TTT GGT ATT AAA AGT TCA TAC ATT AGA CAG TAT CAG CCA   4242
AAA TTT GAG TTA GCA ACA CTG TTT TCT TTA CGA GAG GGT CTC ACC CAA   4290
ATT TAT GGG GAG AAA TCT ATT TCT CAA AAA AAA AAA ATC TTC TTT TAC   4338
AGA AAT GTT GAG TAA GGT GAC ATT TTG AGC GCT AAT AAG CAA AAG AGC   4386
ATG CAG TGC TGT TGA ATA ACC CTC ACT TGG AGA ACC AAG AGA ATC CTG   4434
TCG TTT AAT GCT ATA TTT TAA TTT CAC AAG TTG TTC ATT AAC TG GTA   4482
GAA TGT CAG TCC AAT CTC CAA TGA GAA CAT GAG CAA ATA GAC CTT TCC   4530
```

FIG. 5F

```
AGG TTG AAA GTG AAA CAT ACT GGG TTT CTG TAA GTT TTT CCT CAT GGC    4578
TTC ATC TCT ATC TTT ACT TTC TCT TGA ATA TGC TAC ACA AAG TTC TTT    4626
ATT ACT ACA TAC TAA AGT TTG CAT TCC AGG GAT ATT GAC TGT ACA TAT    4674
TTA TGT ATA TGT ACC ATG TTG TTA CAT GTA AAC AAA CTT CAA TTT GAA    4722
GTG CAG CTA TTA TGT GGT ATC CAT GTG TAT CGA CCA TGT GCC ATA TAT    4770
CAA TTA TGG TCA CTA GAA AGT CTC TTT ATG ATA CTT TTT ATT GTA CTG    4818
TTT TTC ATT TCA CTT GCA AAA TTT TGC AGA ATT CCT CCT TTC TAC CCA    4866
TAA ATT ACA TAT AAT TTT TCT TCT TTA GTC ATG GAG AAC NCC CCC CCA    4914
TCA TCT CAN CCC TAT TAN CTT TCC CAT GTG TAC TGG TAT TAT TAA AAA    4962
GAC ATT TAC ATA CGC AAG TTT TTC ACT GAC AAN CAA GAA TGT TAT TAA    5010
TGT GTA ATA CTG AGC ACN TTT ACT TCT TAA TAA AAA CTT GAT ATA NT     5057
```

FIG. 5G

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
          (A) LENGTH: 866 amino acids
          (B) TYPE:  amino acid
          (C) STRANDEDNESS:  single
          (D) TOPOLOGY:  linear (ii) MOLECULE TYPE:
          (A) DESCRIPTION:  peptide (iii) HYPOTHETICAL:  NO (v) FRAGMENT TYPE: internal fragment (xi) SEQUENCE DESCRIPTION:   SEQ ID NO: 1:

Met Val Asn Ser Ser Arg Val Gln Pro Gln
1               5                  10

Gln Pro Gly Asp Ala Lys Arg Pro Pro Ala
               15                  20

Pro Arg Ala Pro Asp Pro Gly Arg Leu Met
               25                  30

Ala Gly Cys Ala Ala Val Gly Ala Ser Leu
               35                  40

Ala Ala Pro Gly Gly Leu Cys Glu Gln Arg
               45                  50

Gly Leu Glu Ile Glu Met Gln Arg Ile Arg
               55                  60

Gln Ala Ala Ala Arg Asp Pro Pro Ala Gly
               65                  70

Ala Ala Ala Ser Pro Ser Pro Pro Leu Ser
               75                  80

Ser Cys Ser Arg Gln Ala Trp Ser Arg Asp
               85                  90

Asn Pro Gly Glu Glu Glu Ala Glu Glu Glu
               95                 100

Glu Glu Glu Val Glu Gly Glu Glu Gly Gly
              105                 110

Met Val Val Glu Met Asp Val Glu Trp Arg
              115                 120

Pro Gly Ser Arg Arg Ser Ala Ala Ser Ser
              125                 130

Ala Val Ser Ser Val Gly Ala Arg Ser Arg
              135                 140

Gly Leu Gly Gly Tyr His Gly Ala Gly His
              145                 150

Pro Ser Gly Arg Arg Arg Arg Arg Glu Asp
              155                 160

Gln Gly Pro Pro Cys Pro Ser Pro Val Gly
              165                 170

Gly Gly Asp Pro Leu His Arg His Leu Pro
              175                 180

Leu Glu Gly Gln Pro Pro Arg Val Ala Trp
              185                 190

Ala Glu Arg Leu Val Arg Gly Leu Arg Gly
              195                 200

Leu Trp Gly Thr Arg Leu Met Glu Glu Ser
              205                 210

-continued

```
Ser Thr Asn Arg Glu Lys Tyr Leu Lys Ser
            215                 220

Val Leu Arg Glu Leu Val Thr Tyr Leu Leu
            225                 230

Phe Leu Ile Val Leu Cys Ile Leu Thr Tyr
            235                 240

Gly Thr Glu Ala Asp Asn Arg Ser Phe Ile
            245                 250

Phe Tyr Glu Asn Leu Leu Leu Gly Val Pro
            255                 260

Arg Ile Arg Gln Leu Arg Val Arg Asn Gly
            265                 270

Ser Cys Ser Ile Pro Gln Asp Leu Arg Asp
            275                 280

Glu Ile Lys Glu Cys Tyr Asp Val Tyr Glu
            285                 290

Thr Ala Ala Gln Val Ala Ser Leu Lys Lys
            295                 300

Asn Val Trp Leu Asp Arg Gly Thr Arg Ala
            305                 310

Thr Phe Ile Asp Phe Ser Val Tyr Asn Ala
            315                 320

Asn Ile Asn Leu Phe Cys Val Val Arg Leu
            325                 330

Leu Val Glu Phe Pro Ala Thr Gly Gly Val
            335                 340

Ile Pro Ser Trp Gln Phe Gln Pro Leu Lys
            345                 350

Leu Ile Arg Tyr Val Thr Thr Phe Asp Phe
            355                 360

Phe Leu Ala Ala Cys Glu Ile Ile Phe Cys
            365                 370

Phe Phe Ile Phe Tyr Tyr Val Val Glu Glu
            375                 380

Ile Leu Glu Xaa Ile Arg Ile His Lys Leu
            385                 390

His Tyr Phe Arg Xaa Ser Phe Trp Asn Cys
            395                 400

Leu Asp Val Val Ile Val Leu Ser Val
            405                 410

Val Ala Ile Gly Ile Asn Ile Tyr Arg Thr
            415                 420

Ser Asn Val Glu Val Xaa Leu Leu Gln Phe
            425                 430

Leu Xaa Glu Asp Gln Asn Thr Phe Pro Asn
            435                 440

Phe Glu His Leu Ala Tyr Trp Gln Ile Gln
            445                 450

Phe Asn Asn Ile Ala Ala Val Thr Val Phe
            455                 460

Phe Val Trp Ile Lys Leu Phe Lys Phe Ile
            465                 470

Asn Phe Asn Arg Thr Met Ser Gln Leu Ser
```

-continued

```
                475                 480
Thr Thr Met Ser Arg Cys Ala Lys Asp Leu
                485                 490
Phe Gly Phe Ala Ile Met Phe Phe Ile Ile
                495                 500
Phe Leu Ala Tyr Ala Gln Leu Ala Tyr Leu
                505                 510
Val Phe Gly Thr Gln Val Asp Asp Phe Ser
                515                 520
Thr Phe Gln Glu Cys Ile Phe Thr Gln Phe
                525                 530
Arg Ile Ile Leu Gly Asp Ile Asn Phe Ala
                535                 540
Glu Ile Glu Glu Ala Asn Xaa Arg Val Leu
                545                 550
Gly Pro Ile Tyr Phe Thr Thr Phe Val Phe
                555                 560
Phe Met Phe Phe Ile Leu Leu Asn Met Phe
                565                 570
Leu Ala Ile Ile Asn Asp Thr Tyr Ser Glu
                575                 580
Val Lys Ser Asp Leu Xaa Xaa Xaa Ala Gln
                585                 590
Gln Lys Ala Glu Met Glu Leu Ser Asp Leu
                595                 600
Ile Arg Lys Gly Tyr His Lys Ala Leu Val
                605                 610
Lys Leu Lys Leu Lys Lys Asn Thr Val Asp
                615                 620
Asp Ile Ser Glu Ser Leu Arg Gln Gly Gly
                625                 630
Gly Lys Leu Asn Phe Asp Glu Leu Arg Gln
                635                 640
Asp Leu Lys Gly Lys Gly His Thr Asp Ala
                645                 650
Glu Ile Glu Ala Ile Phe Thr Lys Tyr Asp
                655                 660
Gln Asp Gly Asp Gln Glu Leu Thr Glu His
                665                 670
Glu His Gln Gln Met Arg Asp Asp Leu Glu
                675                 680
Lys Glu Arg Glu Asp Leu Asp Leu Asp His
                685                 690
Ser Ser Leu Pro Arg Pro Met Ser Ser Arg
                695                 700
Ser Phe Pro Arg Ser Leu Asp Asp Ser Glu
                705                 710
Glu Asp Asp Asp Glu Asp Ser Gly His Ser
                715                 720
Ser Arg Arg Arg Gly Ser Ile Ser Ser Gly
                725                 730
Val Ser Tyr Glu Glu Phe Gln Val Leu Val
                735                 740
```

```
Arg Arg Val Asp Arg Met Glu His Ser Ile
            745                 750

Gly Ser Ile Val Ser Lys Ile Asp Ala Val
            755                 760

Ile Val Lys Leu Glu Ile Met Glu Arg Ala
            765                 770

Lys Leu Lys Arg Arg Glu Val Leu Gly Arg
            775                 780

Leu Leu Asp Gly Val Ala Glu Asp Glu Arg
            785                 790

Leu Gly Arg Asp Ser Glu Ile His Arg Glu
            795                 800

Gln Met Glu Arg Leu Val Arg Glu Glu Leu
            805                 810

Glu Arg Trp Glu Ser Asp Asp Ala Ala Ser
            815                 820

Gln Ile Ser His Gly Leu Gly Thr Pro Val
            825                 830

Gly Leu Asn Gly Gln Pro Arg Pro Arg Ser
            835                 840

Ser Arg Pro Ser Ser Ser Gln Ser Xaa Thr
            845                 850

Glu Gly Met Glu Gly Ala Gly Gly Asn Gly
            855                 860

Ser Ser Asn Val His Val
            865

(2) INFORMATION FOR SEQ ID NO:2:

(i) SEQUENCE CHARACTERISTICS:
        (A) LENGTH: 523 amino acids
        (B) TYPE:   amino acid
        (C) STRANDEDNESS: single
        (D) TOPOLOGY: linear (ii) MOLECULE TYPE:
         (A) DESCRIPTION: peptide (iii) HYPOTHETICAL: NO (v) FRAGMENT TYPE: internal fragment (xi) SEQUENCE DESCRIPTION: SEQ ID NO: 2:

Phe Leu Ala Lys Glu Glu Ala Arg Lys Val
1               5                   10

Lys Arg Leu His Gly Met Leu Arg Ser Leu
            15                  20

Leu Val Tyr Met Leu Phe Leu Leu Val Thr
            25                  30

Leu Leu Ala Ser Tyr Gly Asp Ala Ser Cys
            35                  40

His Gly His Ala Tyr Xaa Arg Leu Gln Ser
            45                  50

Xaa Xaa Xaa Xaa Xaa Ala Ile Lys Gln Glu
            55                  60

Leu His Ser Arg Ala Phe Leu Ala Ile Thr
            65                  70
```

-continued

```
Arg Ser Glu Glu Leu Trp Pro Trp Met Ala
            75                  80

His Val Leu Leu Pro Tyr Val His Xaa Xaa
            85                  90

Xaa Xaa Xaa Gly Asn Gln Ser Ser Pro Glu
            95                 100

Xaa Xaa Xaa Xaa Xaa Xaa Xaa Xaa Xaa Xaa
           105                 110

Xaa Leu Gly Pro Pro Arg Leu Arg Gln Val
           115                 120

Arg Leu Gln Glu Ala Leu Tyr Pro Asp Pro
           125                 130

Pro Gly Pro Arg Val His Thr Cys Ser Ala
           135                 140

Ala Gly Gly Phe Ser Thr Ser Asp Tyr Asp
           145                 150

Val Gly Trp Glu Ser Pro His Asn Gly Ser
           155                 160

Gly Thr Trp Ala Thr Xaa Xaa Ser Ala Pro
           165                 170

Asp Leu Leu Gly Ala Trp Ser Trp Gly Ser
           175                 180

Cys Ala Val Tyr Asp Ser Gly Gly Tyr Val
           185                 190

Gln Glu Leu Gly Leu Ser Leu Glu Glu Ser
           195                 200

Arg Asp Arg Leu Arg Phe Leu Gln Leu His
           205                 210

Asn Trp Leu Asp Asn Arg Ser Arg Ala Val
           215                 220

Phe Leu Glu Leu Thr Arg Tyr Ser Pro Ala
           225                 230

Val Gly Leu His Ala Ala Val Thr Leu Arg
           235                 240

Leu Glu Phe Pro Ala Ala Gly Arg Ala Leu
           245                 250

Ala Ala Leu Ser Val Arg Pro Phe Ala Leu
           255                 260

Arg Arg Leu Ser Ala Gly Leu Ser Leu Pro
           265                 270

Leu Leu Thr Ser Val Cys Leu Leu Leu Phe
           275                 280

Ala Val His Phe Ala Val Ala Glu Ala Arg
           285                 290

Thr Trp Xaa His Arg Glu Gly Arg Trp Arg
           295                 300

Val Leu Arg Leu Gly Ala Trp Ala Arg Trp
           305                 310

Leu Leu Val Ala Leu Thr Ala Thr Ala
           315                 320

Leu Val Arg Leu Ala Gln Leu Gly Ala Ala
           325                 330

Asp Arg Gln Xaa Xaa Trp Thr Arg Phe Val
```

```
                        335                 340

Arg Gly Arg Pro Arg Arg Phe Thr Ser Phe
                    345                 350

Asp Gln Val Ala Gln Leu Ser Ser Ala Ala
                    355                 360

Arg Gly Leu Ala Ala Ser Leu Leu Phe Leu
                    365                 370

Leu Leu Val Lys Ala Ala Gln Gln Leu Arg
                    375                 380

Phe Val Arg Gln Trp Ser Val Phe Gly Lys
                    385                 390

Thr Leu Cys Arg Ala Leu Pro Glu Leu Leu
                    395                 400

Gly Val Thr Leu Gly Leu Val Val Leu Gly
                    405                 410

Val Ala Tyr Ala Gln Leu Ala Ile Leu Leu
                    415                 420

Val Ser Ser Cys Val Asp Ser Leu Trp Ser
                    425                 430

Val Ala Gln Ala Leu Leu Xaa Xaa Xaa Xaa
                    435                 440

Val Leu Cys Pro Gly Thr Gly Leu Ser Thr
                    445                 450

Leu Cys Pro Ala Glu Ser Trp His Leu Ser
                    455                 460

Pro Leu Leu Cys Val Gly Leu Trp Ala Leu
                    465                 470

Arg Leu Trp Gly Ala Leu Arg Leu Gly Ala
                    475                 480

Val Ile Leu Arg Trp Arg Tyr His Ala Leu
                    485                 490

Arg Gly Glu Leu Tyr Arg Pro Ala Trp Glu
                    495                 500

Pro Gln Asp Tyr Glu Met Val Glu Leu Phe
                    505                 510

Xaa Xaa Xaa Xaa Xaa Xaa Xaa Leu Arg Arg
                    515                 520

Leu Arg Leu (2) INFORMATION FOR SEQ ID NO:3:

(i) SEQUENCE CHARACTERISTICS:
        (A) LENGTH: 399 amino acids
        (B) TYPE:   amino acid
        (C) STRANDEDNESS: single
        (D) TOPOLOGY: linear (ii) MOLECULE TYPE:
        (A) DESCRIPTION: peptide (iii) HYPOTHETICAL: NO (v) FRAGMENT TYPE: internal fragment (xi) SEQUENCE DESCRIPTION: SEQ ID NO: 3:

Glu Asn Arg Lys Met Arg Asp Glu Gln Leu
 1               5                  10
```

-continued

```
Phe Ile Thr Ile Arg Asp Met Leu Cys Phe
            15                  20
Phe Ala Ser Leu Tyr Ile Met Val Met Leu
            25                  30
Thr Tyr Tyr Cys Lys Asp Arg His Gly Tyr
            35                  40
Trp Tyr Gln Leu Glu Met Ser Thr Ile Leu
            45                  50
Asn Ile Asn Gln Lys Asn Tyr Gly Asp Asn
            55                  60
Thr Xaa Phe Met Ser Ile Gln His Ala Asp
            65                  70
Asp Phe Trp Asp Trp Ala Arg Glu Ser Leu
            75                  80
Ala Thr Ala Leu Leu Ala Ser Trp Tyr Asp
            85                  90
Gly Asn Pro Ala Tyr Gly Met Arg Ala Tyr
            95                 100
Met Asn Asp Lys Val Ser Arg Ser Met Gly
           105                 110
Ile Gly Thr Ile Arg Gln Val Arg Thr Lys
           115                 120
Lys Ser Glu Ile Ile Thr Leu Phe Asn Lys
           125                 130
Leu Asp Ser Glu Arg Trp Ile Asp Asp His
           135                 140
Thr Arg Ala Val Ile Ile Glu Phe Ser Ala
           145                 150
Tyr Asn Ala Gln Ile Asn Tyr Phe Ser Val
           155                 160
Val Gln Leu Leu Val Glu Ile Pro Lys Ser
           165                 170
Gly Ile Tyr Leu Pro Asn Ser Trp Val Glu
           175                 180
Ser Val Arg Leu Ile Lys Ser Glu Gly Ser
           185                 190
Asp Gly Thr Val Val Lys Tyr Tyr Glu Met
           195                 200
Leu Tyr Ile Phe Phe Ser Val Leu Ile Phe
           205                 210
Val Lys Glu Ile Val Trp Asn Phe Met Asp
           215                 220
Leu Ile Val Gly Ala Leu Ala Val Ala Ser
           225                 230
Val Leu Ala Tyr Thr Ile Arg Gln Arg Thr
           235                 240
Thr Asn Arg Ala Met Glu Asp Phe Asn Ala
           245                 250
Asn Asn Gly Asn Ser Tyr Ile Asn Leu Thr
           255                 260
Glu Gln Arg Asn Trp Glu Ile Val Phe Ser
           265                 270
Tyr Cys Leu Ala Gly Ala Val Phe Phe Thr
```

```
                        275                 280
Ser Cys Lys Met Ile Arg Ile Leu Arg Phe
                285                 290

Asn Arg Arg Ile Gly Val Leu Ala Ala Thr
                295                 300

Leu Asp Asn Ala Leu Gly Ala Ile Val Ser
                305                 310

Phe Gly Ile Ala Phe Leu Phe Phe Ser Met
                315                 320

Thr Phe Asn Ser Val Leu Tyr Ala Val Leu
                325                 330

Gly Asn Lys Met Gly Gly Tyr Arg Ser Leu
                335                 340

Met Ala Thr Phe Gln Thr Ala Leu Ala Gly
                345                 350

Met Leu Gly Lys Leu Asp Val Thr Ser Ile
                355                 360

Gln Pro Xaa Xaa Xaa Xaa Xaa Ile Ser Gln
                365                 370

Phe Ala Phe Val Val Ile Met Leu Tyr Met
                375                 380

Ile Glu Phe Glu Glu Ile Arg Asn Asp Ser
                385                 390

Glu Lys Gln Thr Asn Asp Tyr Glu Ile
                395
```

(2) INFORMATION FOR SEQ ID NO:4:

(i) SEQUENCE CHARACTERISTICS:
        (A) LENGTH: 363 amino acids
        (B) TYPE: amino acid
        (C) STRANDEDNESS: single
        (D) TOPOLOGY: linear (ii) MOLECULE TYPE:
        (A) DESCRIPTION: peptide (iii) HYPOTHETICAL: NO (v) FRAGMENT TYPE: internal fragment (xi) SEQUENCE DESCRIPTION: SEQ ID NO: 4:

```
Phe Thr Met Val Phe Ser Leu Glu Cys Val
1               5                   10

Leu Lys Val Ile Ala Phe Gly Phe Leu Asn
                15                  20

Tyr Phe Arg Xaa Asp Thr Trp Asn Ile Phe
                25                  30

Asp Phe Ile Thr Val Ile Gly Ser Ile Thr
                35                  40

Glu Ile Ile Leu Thr Asp Ser Lys Leu Val
                45                  50

Asn Thr Ser Gly Xaa Phe Xaa Xaa Xaa Xaa
                55                  60

Xaa Xaa Xaa Xaa Xaa Xaa Xaa Xaa Xaa Xaa
                65                  70

Xaa Asn Met Ser Phe Leu Lys Xaa Xaa Xaa
                75                  80
```

```
Xaa Xaa Xaa Xaa Xaa Xaa Xaa Xaa Leu Phe
                    85                  90

Arg Ala Ala Arg Leu Ile Lys Leu Leu Arg
                    95                  100

Gln Gly Tyr Thr Ile Arg Ile Leu Leu Trp
                    105                 110

Thr Phe Val Gln Ser Phe Lys Ala Leu Pro
                    115                 120

Tyr Val Cys Leu Leu Ile Ala Met Leu Phe
                    125                 130

Phe Ile Tyr Ala Ile Ile Gly Met Gln Val
                    135                 140

Phe Gly Asn Asn Phe Arg Ser Phe Phe Gly
                    145                 150

Ser Leu Met Leu Leu Phe Arg Ser Ala Thr
                    155                 160

Gly Glu Xaa Ala Trp Gln Glu Ile Glu Arg
                    165                 170

Cys Gly Xaa Thr Asp Leu Ala Tyr Val Tyr
                    175                 180

Phe Val Ser Phe Ile Phe Phe Cys Ser Phe
                    185                 190

Leu Met Leu Asn Leu Phe Val Ala Val Ile
                    195                 200

Met Asp Asn Phe Glu Tyr Leu Thr Arg Asp
                    205                 210

Xaa Xaa Xaa Xaa Xaa Xaa Xaa Xaa Xaa Xaa
                    215                 220

Xaa Xaa Xaa Xaa Xaa Xaa Xaa Xaa Xaa Xaa
                    225                 230

Xaa Xaa Xaa Xaa Xaa Xaa Xaa Xaa Xaa Xaa
                    235                 240

Xaa Xaa Xaa Xaa Xaa Xaa Xaa Xaa Xaa Xaa
                    245                 250

Xaa Xaa Xaa Xaa Xaa Xaa Xaa Xaa Xaa Xaa
                    255                 260

Xaa Xaa Xaa Xaa Xaa Xaa Xaa Ile Leu Gly
                    265                 270

Pro His His Leu Asp Xaa Glu Phe Val Arg
                    275                 280

Val Trp Ala Glu Tyr Asp Arg Ala Ala Cys
                    285                 290

Gly Arg Ile His Tyr Thr Glu Met Tyr Glu
                    295                 300

Met Glu Arg Arg Arg Ser Lys Glu Arg Lys
                    305                 310

His Leu Leu Ser Pro Asp Val Ser Arg Cys
                    315                 320

Asn Ser Glu Glu Arg Gly Thr Gln Ala Asp
                    325                 330

Trp Glu Ser Pro Glu Arg Arg Gln Ser Arg
                    335                 340
```

```
Ser Pro Ser Glu Gly Arg Ser Gln Thr Pro
            345                 350

Asn Arg Gln Gly Thr Gly Ser Leu Ser Glu
            355                 360

Ser Ser Ile (2) INFORMATION FOR SEQ ID NO:5:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE:
        (A) DESCRIPTION: peptide (iii) HYPOTHETICAL: NO (xi) SEQUENCE DESCRIPTION: SEQ ID NO: 5:

Glu Ile Ala Ile Phe Thr Lys Tyr Asp Gln
1               5                   10

Asp Gly Asp Gln Glu Leu Thr Glu His Glu
            15                  20

His Gln Gln Met Arg Asp Asp Leu
            25

(2) INFORMATION FOR SEQ ID NO:6:

(i) SEQUENCE CHARACTERISTICS:
        (A) LENGTH: 5057 nucleic acids
        (B) TYPE: nucleic acid
        (C) STRANDEDNESS: single
        (D) TOPOLOGY: linear (ii) MOLECULE TYPE:
        (A) DESCRIPTION: genomic DNA (iii) HYPOTHETICAL: NO (xi) SEQUENCE DESCRIPTION: SEQ ID NO: 6:
```

| | | |
|---|---|---|
| GGCTCCTGAG GCGCACAGCG CCGAGCGCGG CGCCGCGCAC CCGCGCGCCG | 50 |
| GACGCCAGTG ACCGCGATGG TGAACTCCAG TCGCGTGCAG CCTCAGCAGC | 100 |
| CCGGGGACGC CAAGCGGCCG CCCCGCGCCC GCGCGCCGGA CCCGGGCGG | 150 |
| CTGATGGCTG GCTGCGCGGC CGTGGGCGCC AGCCTCGCCG CCCCGGGCGG | 200 |
| CCTCTGCGAG CAGCGGGGCC TGGAGATCGA GATGCAGCGC ATCCGGCAGG | 250 |
| CGGCCGCGCG GGACCCCCCG GCCGGAGCCG CGGCCTCCCC TTCTCCTCCG | 300 |
| CTCTCGTCGT GCTCCCGGCA GGCGTGGAGC CGCGATAACC CCGGCTTCGA | 350 |
| GGCCGAGGAG GAGGAGGAGG AGGTGGAAGG GGAAGAAGGC GGAATGGTGG | 400 |
| TGGAGATGGA CGTAGAGTGG CGCCCGGGCA GCCGGAGGTC GGCCGCCTCC | 450 |
| TCGGCCGTGA GCTCCGTGGG CGCGCGGAGC CGGGGGCTTG GGGGCTACCA | 500 |
| CGGCGCGGGC CACCCGAGCG GGAGGCGGCG CCGGCGAGAG GACCAGGGCC | 550 |
| CGCCGTGCCC CAGCCCAGTC GGCGGCGGGG ACCCGCTGCA TCGCCACCTC | 600 |
| CCCCTGGAAG GGCAGCCGCC CCGAGTGGCC TGGGCGGAGA GGCTGGTTCG | 650 |
| CGGGCTGCGA GGTCTCTGGG GAACAAGACT CATGGAGGAA AGCAGCACTA | 700 |
| ACCGAGAGAA ATACCTTAAA AGTGTTTTAC GGGAACTGGT CACATACCTC | 750 |

```
CTTTTTCTCA TAGTCTTGTG CATCTTGACC TACGGCATGA TGAGCTCCAA          800

TGTGTACTAC TACACCCGGA TGATGTCACA GCTCTTCCTA GACACCCCCG          850

TGTCCAAAAC GGAGAAAACT AACTTTAAAA CTCTGTCTTC CATGGAAGAC          900

TTCTGGAAGT TCACAGAAGG CTCCTTATTG GATGGGCTGT ACTGGAAGAT          950

GCAGCCCAGC AACCAGACTG AAGCTGACAA CCGAAGTTTC ATCTTCTATG         1000

AGAACCTGCT GTTAGGGGTT CCACGAATAC GGCAACTCCG AGTCAGAAAT         1050

GGATCCTGCT CTATCCCCCA GGACTTGAGA GATGAAATTA AGAGTGCTA          1100

TGATGTCTAC TCTGTCAGTA GTGAAGATAG GGCTCCCTTT GGGCCCCGAA         1150

ATGGAACCGC TTGGATCTAC ACAAGTGAAA AAGACTTGAA TGGTAGTAGC         1200

CACTGGGGAA TCATTGCAAC TTATAGTGGA GCTGGCTATT ATCTGGATTT         1250

GTCAAGAACA AGAGAGGAAA CAGCTGCACA AGTTGCTAGC CTCAAGAAAA         1300

ATGTCTGGCT GGACCGAGGA ACCAGGGCAA CTTTTATTGA CTTCTCAGTG         1350

TACAACGCCA ACATTAACCT GTTCTGTGTG GTCAGGTTAT TGGTTGAATT         1400

CCCAGCAACA GGTGGTGTGA TTCCATCTTG GCAATTTCAG CCTTTAAAGC         1450

TGATCCGATA TGTCACAACT TTTGATTTCT TCCTGGCAGC CTGTGAGATT         1500

ATCTTTTGTT TCTTTATCTT TTACTATGTG GTGGAAGAGA TATTGGAAAT         1550

TCGCATTCAC AAACTACACT ATTTCAGGAG TTTCTGGAAT TGTCTGGATG         1600

TTGTGATCGT TGTGCTGTCA GTGGTAGCTA TAGGAATTAA CATATACAGA         1650

ACATCAAATG TGGAGGTGCT ACTACAGTTT CTGGAAGATC AAAATACTTT         1700

CCCCAACTTT GAGCATCTGG CATATTGGCA GATACAGTTC AACAATATAG         1750

CTGCTGTCAC AGTATTTTTT GTCTGGATTA AGCTCTTCAA ATTCATCAAT         1800

TTTAACAGGA CCATGAGCCA GCTCTCGACA ACCATGTCTC GATGTGCCAA         1850

AGACCTGTTT GGCTTTGCTA TTATGTTCTT CATTATTTTC CTAGCGTATG         1900

CTCAGTTGGC ATACCTTGTC TTTGGCACTC AGGTCGATGA CTTCAGTACT         1950

TTCCAAGAGT GTATCTTCAC TCAATTCCGT ATCATTTTGG GCGATATCAA         2000

CTTTGCAGAG ATTGAGGAAG CTAATCGAGT TTTGGGACCA ATTTATTTCA         2050

CTACATTTGT GTTCTTTATG TTCTTCATTC TTTTGAATAT GTTTTTGGCT         2100

ATCATCAATG ATACTTACTC TGAAGTGAAA TCTGACTTGG CACAGCAGAA         2150

AGCTGAAATG GAACTCTCAG ATCTTATCAG AAAGGGCTAC CATAAAGCTT         2200

TGGTCAAACT AAAACTGAAA AAAAATACCG TGGATGACAT TCAGAGAGT          2250

CTGCGGCAAG GAGGAGGCAA GTTAAACTTT GACGAACTTC GACAAGATCT         2300

CAAAGGGAAG GGCCATACTG ATGCAGAGAT TGAGGCAATA TTCACAAAGT         2350

ACGACCAAGA TGGAGACCAA GAACTGACCG AACATGAACA TCAGCAGATG         2400

AGAGACGACT TGGAGAAAGA GAGGGAGGAC CTGGATTTGG ATCACAGTTC         2450

TTTACCACGT CCCATGAGCA GCCGAAGTTT CCCTCGAAGC CTGGATGACT         2500

CTGAGGAGGA TGACGATGAA GATAGCGGAC ATAGCTCCAG AAGGAGGGGA         2550

AGCATTTCTA GTGGCGTTTC TTACGAAGAG TTTCAAGTCC TGGTGAGACG         2600

AGTGGACCGG ATGGAGCATT CCATCGGCAG CATAGTGTCC AAGATTGACG         2650

CCGTGATCGT GAAGCTAGAG ATTATGGAGC GAGCCAAACT GAAGAGGAGG         2700

GAGGTGCTGG AAGGCTGTT  GGATGGGGTG GCCGAGGATG AAAGGCTGGG         2750
```

-continued

| | |
|---|---|
| TCGTGACAGT GAAATCCATA GGGAACAGAT GGAACGGCTA GTACGTGAAG | 2800 |
| AGTTGGAACG CTGGGAATCC GATGATGCAG CTTCCCAGAT CAGTCATGGT | 2850 |
| TTAGGCACGC CAGTGGGACT AAATGGTCAA CCTCGCCCCA GAAGCTCCCG | 2900 |
| CCCATCTTCC TCCCAATCTA CAGAAGGCAT GGAAGGTGCA GGTGGAAATG | 2950 |
| GGAGTTCTAA TGTCCACGTA TGATATGTGT GTTTCAGTAT GTGTGTTTCT | 3000 |
| AATAAGTGAG GAAGTGGCTG TCCTGAATTG CTGTAACAAG CACACTATTT | 3050 |
| ATATGCCCTG ACCACCATAG GATGCTAGTC TTTGTGACCG ATTGCTAATC | 3100 |
| TTCTGCACTT TAATTTATTT TATATAAACT TTACCCATGG TTCAAAGATT | 3150 |
| TTTTTTTCTT TTTCTCATAT AAGAAATCTA GGTGTAAATA TTGAGTACAG | 3200 |
| AAAAAAAATC TTCATGATGT GTATTGAGCG GTACGCCCAG TTGCCACCAT | 3250 |
| GACTGAGTCT TCTCAGTTGA CAATGAAGTA GCCTTTTAAA GCTAGAAAAC | 3300 |
| TGTCAAGGG CTTCTGAGTT TCATTTCCAG TCACAAAAAT CAGTATTGTT | 3350 |
| ATTTTTTTCC AAGAGTGTGA AGGAAAATGG GGCAATTCCT TTCCACTCTG | 3400 |
| GCATAGTTCA TGAGCTTAAT ACATAGCTTT CTTTTAAGAA AGGAGCCTTT | 3450 |
| TTTTTCAACT AGCTTCCTGG GGTAAACTTT TCTAAAAGAT AAAATGGGAA | 3500 |
| GGAACTCCAA ACTATGATAG AATCTGTGTG AATGGTTAAG ATGAATGTTA | 3550 |
| AATACTATGC TTTTTTGTAA GTTGATCGTA TCTGATGTCT GTGGGACTAA | 3600 |
| CTGTATCACT TAATTTTTAC CTTATTTTGG CTCTAATTTG AATAAGCTGA | 3650 |
| GTAAAACCAC CAAAGATCAG TTATAGGATA AAATGGCATC TCTAACCATA | 3700 |
| ACACAGGAGA ATTGGAAGGA GCCCTAAGTT GTCACTCAGT TTAATTTCTT | 3750 |
| TTAATGGTTA GTTTAGCCTA AAGATTTATC TGCATATTCT TTTTCCCATG | 3800 |
| TGGCTCTACT CATTTGCAAC TGAATTTAAT GTTATAACTC ATCTAGTGAG | 3850 |
| ACCAACTTAC TAAATTTTTA GTATGCACTG AAAGTTTTTA TCCAACAATT | 3900 |
| ATGTTCATTT TAAGCAAAAT TTTAAGAAAG TTTTGAAATT CATAAAGCAT | 3950 |
| TTGGTTTTAA ACTATTTTAA GAATATAGTA CTCGGTCAGG TATGNNNCAC | 4000 |
| GCCTGTAATC CCAGCACTTT GGGAGGCCGA ACAGGCGAA TCACTTGAGC | 4050 |
| CCAGGAGTTC AAGACCAACA TGGGCAATGT GGCGAAACTC CATCTCTACA | 4100 |
| AAAAATGCAA AAATAAAAAA TATAGTACTC AAGTATTCTT GATCCTGTGT | 4150 |
| TTCAAAACTA GAATTTGTAA TGCAAATGGA GCTCAGTCTA ATAAAAAAGA | 4200 |
| GGTTTTGGTA TTAAAAGTTC ATACATTAGA CAGTATCAGC CAAAATTTGA | 4250 |
| GTTAGCAACA CTGTTTTCTT TACGAGAGGG TCTCACCCAA ATTTATGGGG | 4300 |
| AGAAATCTAT TTCTCAAAAA AAAAAAATCT TCTTTTACAG AAATGTTGAG | 4350 |
| TAAGGTGACA TTTTGAGCGC TAATAAGCAA AAGAGCATGC AGTGCTGTTG | 4400 |
| AATAACCCTC ACTTGGAGAA CCAAGAGAAT CCTGTCGTTT AATGCTATAT | 4450 |
| TTTAATTTCA CAAGTTGTTC ATTTAACTGG TAGAATGTCA GTCCAATCTC | 4500 |
| CAATGAGAAC ATGAGCAAAT AGACCTTTCC AGGTTGAAAG TGAAACATAC | 4550 |
| TGGGTTTCTG TAAGTTTTTC CTCATGGCTT CATCTCTATC TTTACTTTCT | 4600 |
| CTTGAATATG CTACACAAAG TTCTTTATTA CTACATACTA AAGTTTGCAT | 4650 |
| TCCAGGGATA TTGACTGTAC ATATTTATGT ATATGTACCA TGTTGTTACA | 4700 |

```
TGTAAACAAA CTTCAATTTG AAGTGCAGCT ATTATGTGGT ATCCATGTGT        4750

ATCGACCATG TGCCATATAT CAATTATGGT CACTAGAAAG TCTCTTTATG        4800

ATACTTTTTA TTGTACTGTT TTTCATTTCA CTTGCAAAAT TTTGCAGAAT        4850

TCCTCCTTTC TACCCATAAA TTACATATAA TTTTTCTTCT TTAGTCATGG        4900

AGAACNCCCC CCCATCATCT CANCCCTATT ANCTTTCCCA TGTGTACTGG        4950

TATTATTAAA AAGACATTTA CATACGCAAG TTTTTCACTG ACAANCAAGA        5000

ATGTTATTAA TGTGTAATAC TGAGCACNTT TACTTCTTAA TAAAAACTTG        5050

ATATANT                                                       5057
```

(2) INFORMATION FOR SEQ ID NO:7:

(i) SEQUENCE CHARACTERISTICS:
        (A) LENGTH: 968 amino acids
        (B) TYPE: amino acid
        (C) STRANDEDNESS: single
        (D) TOPOLOGY: linear (ii) MOLECULE TYPE:
        (A) DESCRIPTION: peptide (iii) HYPOTHETICAL: NO (xi) SEQUENCE DESCRIPTION: SEQ ID NO: 7:

```
Met Val Asn Ser Ser Arg Val Gln Pro Gln Gln Pro Gly Asp Ala Lys
  1               5                  10                  15

Arg Pro Pro Ala Pro Arg Ala Pro Asp Pro Gly Arg Leu Met Ala Gly
                 20                  25                  30

Cys Ala Ala Val Gly Ala Ser Leu Ala Ala Pro Gly Gly Leu Cys Glu
             35                  40                  45

Gln Arg Gly Leu Glu Ile Glu Met Gln Arg Ile Arg Gln Ala Ala Ala
 50                  55                  60

Arg Asp Pro Pro Ala Gly Ala Ala Ala Ser Pro Ser Pro Pro Leu Ser
 65                  70                  75                  80

Ser Cys Ser Arg Gln Ala Trp Ser Arg Asp Asn Pro Gly Phe Glu Ala
                 85                  90                  95

Glu Glu Glu Glu Glu Glu Val Glu Gly Glu Glu Gly Gly Met Val Val
            100                 105                 110

Glu Met Asp Val Glu Trp Arg Pro Gly Ser Arg Arg Ser Ala Ala Ser
            115                 120                 125

Ser Ala Val Ser Ser Val Gly Ala Arg Ser Arg Gly Leu Gly Gly Tyr
130                 135                 140

His Gly Ala Gly His Pro Ser Gly Arg Arg Arg Arg Arg Glu Asp Gln
145                 150                 155                 160

Gly Pro Pro Cys Pro Ser Pro Val Gly Gly Asp Pro Leu His Arg
                165                 170                 175

His Leu Pro Leu Glu Gly Gln Pro Pro Arg Val Ala Trp Ala Glu Arg
                180                 185                 190

Leu Val Arg Gly Leu Arg Gly Leu Trp Gly Thr Arg Leu Met Glu Glu
            195                 200                 205

Ser Ser Thr Asn Arg Glu Lys Tyr Leu Lys Ser Val Leu Arg Glu Leu
210                 215                 220

Val Thr Tyr Leu Leu Phe Leu Ile Val Leu Cys Ile Leu Thr Tyr Gly
225                 230                 235                 240

Met Met Ser Ser Asn Val Tyr Tyr Tyr Thr Arg Met Met Ser Gln Leu
                245                 250                 255
```

```
Phe Leu Asp Thr Pro Val Ser Lys Thr Glu Lys Thr Asn Phe Lys Thr
            260                 265                 270

Leu Ser Ser Met Glu Asp Phe Trp Lys Phe Thr Glu Gly Ser Leu Leu
        275                 280                 285

Asp Gly Leu Tyr Trp Lys Met Gln Pro Ser Asn Gln Thr Glu Ala Asp
    290                 295                 300

Asn Arg Ser Phe Ile Phe Tyr Glu Asn Leu Leu Leu Gly Val Pro Arg
305                 310                 315                 320

Ile Arg Gln Leu Arg Val Arg Asn Gly Ser Cys Ser Ile Pro Gln Asp
                325                 330                 335

Leu Arg Asp Glu Ile Lys Glu Cys Tyr Asp Val Tyr Ser Val Ser Ser
            340                 345                 350

Glu Asp Arg Ala Pro Phe Gly Pro Arg Asn Gly Thr Ala Trp Ile Tyr
        355                 360                 365

Thr Ser Glu Lys Asp Leu Asn Gly Ser Ser His Trp Gly Ile Ile Ala
    370                 375                 380

Thr Tyr Ser Gly Ala Gly Tyr Tyr Leu Asp Leu Ser Arg Thr Arg Glu
385                 390                 395                 400

Glu Thr Ala Ala Gln Val Ala Ser Leu Lys Lys Asn Val Trp Leu Asp
                405                 410                 415

Arg Gly Thr Arg Ala Thr Phe Ile Asp Phe Ser Val Tyr Asn Ala Asn
            420                 425                 430

Ile Asn Leu Phe Cys Val Val Arg Leu Leu Val Glu Phe Pro Ala Thr
        435                 440                 445

Gly Gly Val Ile Pro Ser Trp Gln Phe Gln Pro Leu Lys Leu Ile Arg
    450                 455                 460

Tyr Val Thr Thr Phe Asp Phe Phe Leu Ala Ala Cys Glu Ile Ile Phe
465                 470                 475                 480

Cys Phe Phe Ile Phe Tyr Tyr Val Val Glu Ile Leu Glu Ile Arg
                485                 490                 495

Ile His Lys Leu His Tyr Phe Arg Ser Phe Trp Asn Cys Leu Asp Val
            500                 505                 510

Val Ile Val Val Leu Ser Val Val Ala Ile Gly Ile Asn Ile Tyr Arg
        515                 520                 525

Thr Ser Asn Val Glu Val Leu Leu Gln Phe Leu Glu Asp Gln Asn Thr
    530                 535                 540

Phe Pro Asn Phe Glu His Leu Ala Tyr Trp Gln Ile Gln Phe Asn Asn
545                 550                 555                 560

Ile Ala Ala Val Thr Val Phe Phe Val Trp Ile Lys Leu Phe Lys Phe
                565                 570                 575

Ile Asn Phe Asn Arg Thr Met Ser Gln Leu Ser Thr Thr Met Ser Arg
            580                 585                 590

Cys Ala Lys Asp Leu Phe Gly Phe Ala Ile Met Phe Phe Ile Ile Phe
        595                 600                 605

Leu Ala Tyr Ala Gln Leu Ala Tyr Leu Val Phe Gly Thr Gln Val Asp
    610                 615                 620

Asp Phe Ser Thr Phe Gln Glu Cys Ile Phe Thr Gln Phe Arg Ile Ile
625                 630                 635                 640

Leu Gly Asp Ile Asn Phe Ala Glu Ile Glu Glu Ala Asn Arg Val Leu
                645                 650                 655

Gly Pro Ile Tyr Phe Thr Thr Phe Val Phe Phe Met Phe Phe Ile Leu
            660                 665                 670
```

-continued

```
Leu Asn Met Phe Leu Ala Ile Ile Asn Asp Thr Tyr Ser Glu Val Lys
        675                 680                 685

Ser Asp Leu Ala Gln Gln Lys Ala Glu Met Glu Leu Ser Asp Leu Ile
    690                 695                 700

Arg Lys Gly Tyr His Lys Ala Leu Val Lys Leu Lys Leu Lys Lys Asn
705                 710                 715                 720

Thr Val Asp Asp Ile Ser Glu Ser Leu Arg Gln Gly Gly Lys Leu
                725                 730                 735

Asn Phe Asp Glu Leu Arg Gln Asp Leu Lys Gly Lys Gly His Thr Asp
                740                 745                 750

Ala Glu Ile Glu Ala Ile Phe Thr Lys Tyr Asp Gln Asp Gly Asp Gln
            755                 760                 765

Glu Leu Thr Glu His Glu His Gln Gln Met Arg Asp Asp Leu Glu Lys
        770                 775                 780

Glu Arg Glu Asp Leu Asp Leu Asp His Ser Ser Leu Pro Arg Pro Met
785                 790                 795                 800

Ser Ser Arg Ser Phe Pro Arg Ser Leu Asp Asp Ser Glu Glu Asp Asp
                805                 810                 815

Asp Glu Asp Ser Gly His Ser Ser Arg Arg Gly Ser Ile Ser Ser
                820                 825                 830

Gly Val Ser Tyr Glu Glu Phe Gln Val Leu Val Arg Arg Val Asp Arg
        835                 840                 845

Met Glu His Ser Ile Gly Ser Ile Val Ser Lys Ile Asp Ala Val Ile
850                 855                 860

Val Lys Leu Glu Ile Met Glu Arg Ala Lys Leu Lys Arg Arg Glu Val
865                 870                 875                 880

Leu Gly Arg Leu Leu Asp Gly Val Ala Glu Asp Glu Arg Leu Gly Arg
                885                 890                 895

Asp Ser Glu Ile His Arg Glu Gln Met Glu Arg Leu Val Arg Glu Glu
                900                 905                 910

Leu Glu Arg Trp Glu Ser Asp Asp Ala Ala Ser Gln Ile Ser His Gly
            915                 920                 925

Leu Gly Thr Pro Val Gly Leu Asn Gly Gln Pro Arg Pro Arg Ser Ser
    930                 935                 940

Arg Pro Ser Ser Ser Gln Ser Thr Glu Gly Met Glu Gly Ala Gly Gly
945                 950                 955                 960

Asn Gly Ser Ser Asn Val His Val
                965
```

(2) INFORMATION FOR SEQ ID NO:8:

(i) SEQUENCE CHARACTERISTICS:
        (A) LENGTH: 19 nucleic acids
        (B) TYPE: nucleic acid
        (C) STRANDEDNESS: single
        (D) TOPOLOGY: linear (ii) MOLECULE TYPE:
        (A) DESCRIPTION: genomic DNA (iii) HYPOTHETICAL: NO (xi) SEQUENCE DESCRIPTION: SEQ ID NO: 8:

GGGCTACCAT AAAGCTTTG                                                19

(2) INFORMATION FOR SEQ ID NO:9:

(i) SEQUENCE CHARACTERISTICS:

```
        (A) LENGTH: 20 nucleic acids
        (B) TYPE: nucleic acid
        (C) STRANDEDNESS: single
        (D) TOPOLOGY: linear (ii) MOLECULE TYPE:
        (A) DESCRIPTION: genomic DNA (iii) HYPOTHETICAL: NO (xi) SEQUENCE DESCRIPTION: SEQ ID NO: 9:

GTTCATGTTC GATCAGTTCT                                               20

(2) INFORMATION FOR SEQ ID NO:10:

(i) SEQUENCE CHARACTERISTICS:
        (A) LENGTH: 23 nucleic acids
        (B) TYPE: nucleic acid
        (C) STRANDEDNESS: single
        (D) TOPOLOGY: linear (ii) MOLECULE TYPE:
        (A) DESCRIPTION: genomic DNA (iii) HYPOTHETICAL: NO (xi) SEQUENCE DESCRIPTION: SEQ ID NO: 10:

GGGCTAGAAA TACTCTTATC ACC                                           23

(2) INFORMATION FOR SEQ ID NO:11:

(i) SEQUENCE CHARACTERISTICS:
        (A) LENGTH: 20 nucleic acids
        (B) TYPE: nucleic acid
        (C) STRANDEDNESS: single
        (D) TOPOLOGY: linear (ii) MOLECULE TYPE:
        (A) DESCRIPTION: genomic DNA (iii) HYPOTHETICAL: NO (xi) SEQUENCE DESCRIPTION: SEQ ID NO: 11:

GCCTCAAGTG TTCCACTGAT                                               20

(2) INFORMATION FOR SEQ ID NO:12:

(i) SEQUENCE CHARACTERISTICS:
        (A) LENGTH: 22 nucleic acids
        (B) TYPE: nucleic acid
        (C) STRANDEDNESS: single
        (D) TOPOLOGY: linear (ii) MOLECULE TYPE:
        (A) DESCRIPTION: genomic DNA (iii) HYPOTHETICAL: NO (xi) SEQUENCE DESCRIPTION: SEQ ID NO: 12:

AGGTTTTTCT GGGTAACCCT AG                                            22
```

POLYCYSTIC KIDNEY DISEASE PKD2 GENE AND USES THEREOF

This is a continuation of U.S. application Ser. No. 08/651,999, filed May 23, 1996, now U.S. Pat. No. 6,031,088 the contents of which are hereby incorporated by reference.

STATEMENT OF GOVERNMENT INTEREST

This invention was made with government support under NIH Grant Nos. DK48383 and DK02015. As such, the government has certain rights in this invention.

BACKGROUND OF THE INVENTION

This invention is based upon the discovery by the inventors of the PKD2 gene associated with Autosomal Dominant Polycystic Kidney Disease ("ADPKD"), the "PKD2 gene" or "PKD2", and a novel protein encoded by this gene. The discovery of the PKD2 gene and the protein encoded by the gene will have important implications in the diagnosis and treatment of ADPKD caused by defects in the PKD2 gene.

ADPKD is a genetically heterogeneous disorder that affects approximately 500,000 Americans and five million individuals world wide, and accounts for 8 to 10% of all end stage renal disease (ESRD) worldwide (Gabow, P. A. *N. Eng. J. Med.* 329:332 (1993)). Its principal clinical manifestation is bilateral renal cysts that result in chronic renal failure in about 45% of affected individuals by age 60 (Gabow, P. A., supra). Hypertension and liver cysts are common, and the involvement of other organ systems (Gabow, P. A., et al. *Kidney Int.* 38:1177 (1990); Chapman, A. B., et al. *N. Eng. J. Med.* 327:916 (1992); Hossack, K. F., et al. *N. Eng. J. Med.* 319:907 (1988); Torres, V. E., et al. *Am. J. Kidney Dis.* 22:513 (1993); Huston, J., et al. *J. Am. Soc. Nephrol.* 3:1871 (1993); Somlo, S., et al. *J. Am. Soc. Nephrol.* 4:1371 (1993)) lends support to the view that polycystic kidney disease is a systemic disorder (Gabow, P. A., supra).

To date, most forms of ADPKD have been associated with two genes, PKD1 and PKD2. The full genomic structure and cDNA sequence for the PKD1 gene has been identified (The International Polycystic Kidney Disease Consortium, *Cell* 81:289 (1995); The American PKD1 Consortium, *Hum. Mol. Genet.* 4:575 (1995)). Mutations in the PKD1 gene are suspected of causing 80–90% of all cases of ADPKD. The PKD2 gene has been localized on chromosome 4q21-23 and accounts for approximately 15% of affected families (Kimberling, W. J., et al. *Genomics* 18:467 (1993); Peters, D. J. M. and L. A. Sandkuijl *Contrib. Nephrol.* 97:128 (1992)). Prior to the present invention, however, the PKD2 gene had not been identified.

SUMMARY OF THE INVENTION

The present invention provides a purified and isolated wild type PKD2 gene, as well as mutated forms of this gene. The present invention also provides one or more single-stranded nucleic acid probes which specifically hybridize to the wild type PKD2 gene or the mutated PKD2 gene, and mixtures thereof, which may be formulated in kits, and used in the diagnosis of ADPKD associated with the mutated PKD2 gene.

The present invention also provides a vector comprising nucleic acid encoding an active PKD2 protein, a cell stably transformed with this vector, as well as a method for producing recombinant, active PKD2 protein. A purified, active PKD2 protein is also provided by the present invention. In addition, the present invention provides an antibody immunoreactive with a wild type PKD2 protein, as well as an antibody immunoreactive with a mutant PKD2 protein, which may be formulated in kits, and used in the diagnosis of ADPKD associated with the mutated PKD2 gene.

The present invention further provides a method for diagnosing ADPKD caused by a mutated PKD2 gene in an adult subject suspected of having the disease comprising detecting the presence of a mutated PKD2 gene in nucleic acid of the subject. The present invention still further provides a method for treating ADPKD caused by a mutated PKD2 gene in a subject in need of such treatment comprising the delivery and expression of a functional PKD2 gene into a sufficient number of cells of the subject to treat the disease. A stem cell which expresses the PKD2 gene introduced therein through viral transduction, homologous recombination or transfection is also provided by the invention.

In addition, the present invention provides a recombinant viral vector for treating a defect in the PKD2 gene in a target cell comprising (a) the nucleic acid of or corresponding to at least a portion of the genome of a virus, which portion is capable of directing the infection of the target cell, and (b) a PKD2 gene operably linked to the viral nucleic acid and capable of being expressed as a functional gene product in the target cell.

Finally, the present invention provides a vector and an embryonic stem cell each of which comprises a mutated PKD2 gene, a non-human, transgenic animal whose germ and somatic cells contain a mutated PKD2 gene sequence introduced into said animal, or an ancestor thereof, at an embryonic stage, as well as a method for producing the non-human, transgenic animal.

Additional objects of the invention will be apparent from the description which follows.

BRIEF DESCRIPTION OF THE FIGURES

FIG. 1A represents the subset of STSs from the high density map of the PKD2 region showing polymorphic loci flanking the interval. JSTG3 and AICA1 are two of nine microsatellite markers in this region developed previously. SPP1 (osteopontin, STS4-1078) and D4S1171 were used to screen the P1 library as described in Materials and Methods. Other sources of STSs include published linkage maps and genome center databases. cen, centromere; tel telomere. Distances are in Morgans along chromosome 4.

FIG. 1B shows representative mega-YACs (Cohen, D., et al. *Nature* 366:698 (1993)), and their STS content, forming a contig around the PKD2 region.

FIG. 1C shows the minimum tiling path of the cosmid and P1 contig in the PKD2 region. Clone names beginning with "c" and "p" refer to cosmid and P1 clones, respectively; addresses are from the original arrayed libraries. The clones containing JSTG3 and AICA1 are shown; a single gap of <40 kb is indicated by the arrow.

FIG. 1D shows the detail of the portion of the contig containing the PKD2 candidate gene, cTM-4.

FIG. 1E shows overlapping map of nine cDNA clones for cTM-4 and a composite schematic at the bottom. Clones K1-1 and K1-5 are from the adult kidney library; clones yj63h09 and yc93g07 were identified by GenBank searching and are from the normalized infant brain library (Soares, M. B., et al. *Proc. Natl. Acad. Sci. USA* 91: 9228 (1994)); all other clones are from the fetal brain library. Shaded areas represent chimeric portions of clones.

FIG. 4A depicts the deduced amino acid sequence of PKD2 (SEQ ID NO:1) (cTM-4) (GenBank accession: gb|U50928) in alignment with PKD1 (SEQ ID NO:2) (gb|U24497), the C. elegans homolog of PKD1 (SEQ ID NO:3) (ZK945.9; swiss|Q09624) and VACCα1E-1 (SEQ ID NO:4) (pir|B54972) using BESTFIT (Program Manual for the Wisconsin Package, Version 8, September 1994): identity to cTM-4, |; similarity to cTM-4, :. Numbers in parentheses refer to amino acids in respective sequences. Putative transmembrane domains, tm1 to tm6. Predicted N-glycosylation sites, *. Potential phosphorylation sites with strong consensus sequences: protein kinase C, +; cGMP dependent kinase, open square (Ser 826 is also consistent with a protein kinase A site); casein kinase, open circle. The sites of the nonsense mutations (FIG. 3) are indicated by arrows labeled with the respective family numbers. The EF-hand domain is indicated by the dashed line.

FIG. 4B shows alignment of the EF-hand domain (SEQ ID NO:5) with the EF-hand test sequence. The residues E, G, I, and E, the latter being a $Ca^{2+}$ coordination vertex, are the expected residues at the indicated positions in the EF-hand. Positions indicated as "n" are expected to have hydrophobic amino acids (L, I, V, F, M); those denoted with * should be oxygen-containing amino acids (D, N, E, Q, S, T) comprising the remainder of coordination vertices for $Ca^{2+}$ binding; the −Y vertex can be any amino acid. The Leu (L) in PKD2 in place of the Ile (I) is likely a permissible substitution; PKD2 has Gln (Q) in place of the consensus Gly (G) as is the case with EF-hand domains in the α1 $Na^+$ channels.

FIGS. 5A–G represents the nucleotide sequence (SEQ ID NO:6) of the PKD2 gene and the deduced amino acid sequence (SEQ ID NO:7) for PKD2.

DETAILED DESCRIPTION OF THE INVENTION

Figure 2:
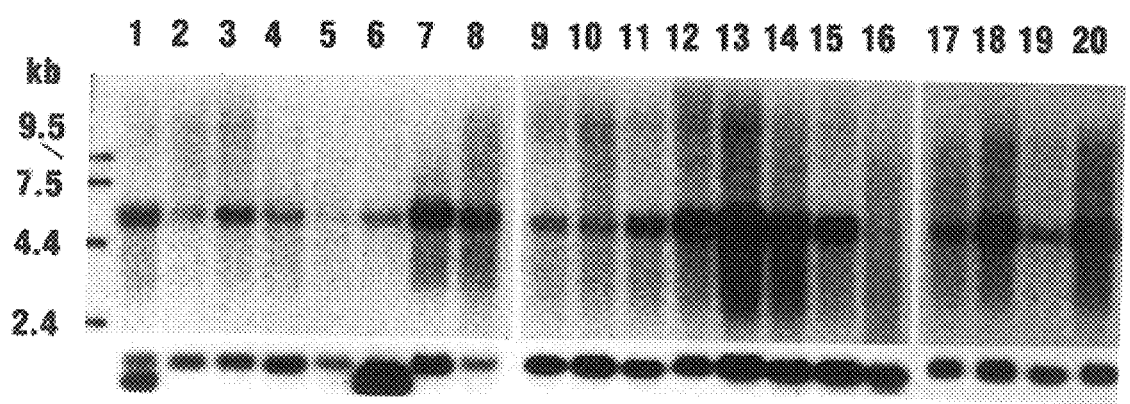
FIG. 2 represents expression of the PKD2 candidate gene. Insert from cTM-4B3-3 (FIG. 1E) was used as a hybridization probe on mRNA blots containing human tissues (Clonetech, Palo Alto, Calif.). Hybridization was performed without pre-competition and a final wash stringency of 0.5X SSC, 0.1% SDS at 65° C. Tissues in numbered lanes are: (1) heart, (2) brain, (3) placenta, (4) lung, (5) liver, (6) skeletal muscle, (7) kidney, (8) pancreas, (9) spleen, (10) thymus, (11) prostate, (12) testis, (13) ovary, (14) small intestine, (15) colon, (16) leukocytes, (17) fetal brain, (18) fetal lung, (19) fetal liver, (20) fetal kidney. At bottom, β-actin hybridization to the same blots is used to compare relative mRNA loading within each blot.

The present invention provides a purified and isolated wild type PKD2 nucleic acid, as well as mutated forms of this nucleic acid. As used herein, the "wild type PKD2 nucleic acid" is the normal form of the gene which expresses an enzymatically active gene product, and includes degenerate forms. The "mutated PKD2 nucleic acid" is the mutated form of the normal PKD2 gene, which contains one or more deletion, insertion, point or rearrangement mutations, or a combination thereof, that may render the gene product expressed by the mutated PKD2 gene nonfunctional or nonexistent. As used herein, "nucleic acid" may be genomic DNA, cDNA or RNA.

The present invention also provides single-stranded nucleic acid probes and mixtures thereof for use in diagnosing ADPKD caused by a mutated PKD2 gene. The nucleic acid probes may be DNA, cDNA, or RNA, and may be prepared from the mutated and/or wild type PKD2 gene. The probes may be the full length sequence of PKD2 gene, or fragments thereof. Typical probes are 12 to 40 nucleotides in length. Generally, the probes are complementary to the PKD2 gene coding sequences, although probes to introns are also contemplated. The probes may be synthesized using an oligonucleotide synthesizer such as Applied Biosystems Model 392 DNA/RNA synthesizer, and may be labeled with a detectable marker such as a fluorescence, enzyme or radiolabeled markers including $^{32}P$ and biotin, and the like. Combinations of two or more labelled probes corresponding to different regions of the PKD2 gene also may be included in kits to allow for the detection and/or analysis of the PKD2 gene by hybridization.

The present invention also provides a vector comprising nucleic acid encoding an active PKD2 protein, as well as a cell stably transformed with the vector. The vector may be any plasmid, viral-derived nucleic acid, lytic bacteriophage derived from phage lambda, cosmid, filamentous single-stranded bacteriophage such as M13, and the like, for cloning nucleic acid or introducing the nucleic acid into a cell for expression. The cell may be eukaryotic or prokaryotic. Suitable host cells include but are not limited to bacterial cells such as E. coli, Bacillus subtilis, Agrobacterium tumefaciens, Bacillus subtilis, Agrobacterium tumefaciens, Bacillus megaterium, eukaryotic cells such as Pichia pastoris, Chlamydomonas reinhardtii, Cryptococcus neoformans, Neurospora crassa, Podospora anserina, Saccharomyces cerevisiae, Saccharomyces pombe, Uncinula necator, cultured insect cells, cultured chicken fibroblasts, cultured hamster cells, cultured human cells such as HT1080, MCF7, 143B and cultured mouse cells such as EL4 and NIH3T3 cells. Such expression systems may be used to produce a recombinant, active PKD2 protein by culturing a cell transformed with a vector comprising a nucleic acid encoding an active PKD2 protein, and recovering PKD2 protein from the culture.

The present invention also provides a purified active PKD2 protein. The protein may be the wild type protein or an analogue thereof. As used herein, "analogue" means functional variants of the wild type protein, and includes PKD2 proteins isolated from mammalian sources other than human, as well as functional variants thereof. The protein also may be isolated from native cells or recombinantly produced.

The present invention also provides antibodies immunoreactive with the protein expressed by the wild type PKD2 gene (and analogues thereof), as well as antibodies immunoreactive with the protein expressed by the mutated PKD2 gene. The antibodies may be polyclonal or monoclonal and are produced by standard techniques. The antibodies may be labeled with standard detectable markers (e.g. chemiluminescent detection systems and radioactive labels such as $^{125}I$) for detecting the wild type and mutated PKD2 genes. The antibodies also may be presented in kits with detectable labels and other reagents and buffers for such detection.

The present invention also provides a method for diagnosing ADPKD in a subject comprising detecting the presence of a mutated PKD2 gene in nucleic acid of the subject. The method may be used to determine whether persons in the population at large have ADPKD, for identifying persons at risk in developing the disease, i.e. relatives of persons with ADPKD, as well as for confirming diagnosis of ADPKD. The method also is useful for diagnosing ADPKD before clinical manifestations of the disease, i.e. the formation of cysts. Accordingly, as used herein, "subject" may be an embryo, fetus, newborn, infant or adult.

The presence of the mutated PKD2 gene may be detected by procedures known in the art including but not limited to standard sequencing techniques (e.g. dideoxy chain termination), restriction enzyme digestion analysis, hybridization with one or more probes hybridizable to the mutated and/or wild type PKD2 gene using standard procedures such as Southern blot analysis, polymerase chain reaction using sense and antisense primers prepared from the mutated and/or wild type PKD2 genes, and combinations thereof.

The presence of the mutated PKD2 gene also may be detected by detecting expression of the gene product of the gene. Such expression products include both mRNA as well as the protein product itself. mRNA expression may be detected by standard sequencing techniques, hybridization with one or more probes hybridizable to the mutated and/or wild type PKD2 mRNA using standard procedures such as Northern blot analyses, dot and slot hybridization, S1 nuclease assay, or ribonuclease protection assays, polymerase chain reaction using sense and antisense primers prepared from the mutated and/or wild type PKD2 genes, and combinations thereof. The protein may be detected using antibodies to the protein expressed by the mutated PKD2 gene and/or the wild type PKD2 gene by procedures known in the art including but not limited to immunoblotting, immunoprecipitation, solid phase radioimmunoassay (e.g. competition RIAs, immobilized antigen or antibody RIAs, or double antibody RIAs), enzyme-linked immunoabsorbent assay, and the like.

The present invention also provides a method for treating ADPKD caused by a mutated PKD2 gene in a subject in need of such treatment comprising the delivery and expression of a functional PKD2 gene into a sufficient number of cells of the subject, preferably bone marrow stem cells, to treat ADPKD in the subject. As used herein, "functional PKD2 gene" is a gene which when incorporated into a cell's nucleic acid expresses a functional gene product, and includes the wild type PKD2 gene as well as variations thereof. The delivery and expression of the functional PKD2 gene may be accomplished by introducing the functional PKD2 gene into the cells or by correcting the mutation(s) in the subject's PKD2 gene.

The functional PKD2 gene may be delivered into the subject's cells by a number of procedures known to one skilled in the art, e.g. electroporation, DEAE dextran, cationic liposome fusion (using both monocationic and polycationic lipids), protoplast fusion, DNA coated microprojectile bombardment, injection with recombinant replication-defective retroviruses, homologous recombination, and the like. Accordingly, a stem cell which expresses the PKD2 gene introduced therein through viral transduction, homologous recombination, or transfection is also provided by the present invention.

The present invention also provides a recombinant viral vector for treating a defect in the PKD2 gene in a target cell comprising (a) the nucleic acid of or corresponding to at least a portion of the genome of a virus, which portion is capable of directing the infection of the target cell, and (b) a functional PKD2 gene operably linked to the viral nucleic acid and capable of being expressed as a functional gene product in the target cell. The recombinant viral vectors of the present invention may be derived from a variety of viral nucleic acids known to one skilled in the art, e.g. the genomes of HSV, adenovirus, adeno-associated virus, Semi-liki Forest virus, vaccinia virus, and other retroviruses or DNA viruses.

The present invention also provides a vector for use in preparing a non-human, transgenic animal comprising a mutated PKD2 gene which is capable of introducing the mutated PKD2 gene in at least some embryonic cells to which the vector is introduced, an embryonic stem cell comprising a mutated PKD2 gene which has been integrated into the cell following transduction with the vector above, as well as a non-human transgenic animal of ADPKD which would be useful for studying ADPKD. The mutated PKD2 gene may be integrated into the germ line of a non-human animal such as a mouse, rat, goat, sheep or other non-human species in order to obtain a transgenic animal model by methods known in the art (see Alberts, B., et al. *Molecular Biology of the Cell,* 2d. Garland Publ. Inc., New York and London, pp. 267–269 (1989)). For example, nucleic acid encoding the mutated PKD2 protein can be inserted into the genome of a replication-defective virus such as HSV or a retrovirus or transposen and the resultant construct injected into embryonic stem cells. Alternatively, the transgenic animal may be made by injecting nucleic acid into the male pronucleus of a fertilized egg of a nonhuman animal, transplanting the "transgenic embryo" into a pseudopregnant female and then analyzing offspring for the presence of the injected nucleic acid in their genome.

The present invention is described in the following Experimental Details Section, which is set forth to aid in an understanding of the invention, and should not be construed to limit in any way the invention as defined in the claims which follow thereafter.

EXPERIMENTAL DETAILS SECTION

A. Materials and Methods

Cosmid and P1 Contig Construction. Cosmid and P1 contig construction was guided by the existing YAC contig (Mochizuki, T., et al., unpublished observations; Veldhuisen, B., et al., unpublished observations). Cosmid clones were obtained by hybridization screening of the human chromosome 4-specific cosmid library (Riess, O., et al. *Cytogenet. Cell Genet.* 65:238 (1994); Ioannou, P. A., et al. *Nature Genetics* 6:84 (1994)). The probes used for hybridization were: 1) pooled Alu products from mega-YAC 967d1, 2) end sequences from cosmid or P1 clones mapping into the region, and 3) internal restriction fragments from the YAC, P1 and cosmid clones. All hybridization probes were $\alpha^{32}$P-dCTP labeled by standard techniques. Human repetitive sequences were pre-competed with 30–80 μg of $C_ot$-1 DNA using the manufacturer's portocol (Gibco/BRL, Gaithsburg, Md.). Hybridization was carried out in Church-Gilbert buffer. The P1 library (Riess, O., et al., supra; Ioannou, P. A., et al., supra) was screened by PCR from colony pools of each 384-well plate using STS4-1078 (SPP1) and D4S1171. Cosmid and P1 clones mapping into the PKD2 interval were screened for STS content to anchor positive clones onto the YAC contig. Overlap relationships among the clones were established by Eco RI fingerprint analysis and by hybridization.

Screening of cDNA Clones. $6 \times 10^5$ plaques of oligo-dT and random primed human fetal brain (Stratagene #936206) and adult kidney (Clonetech #HL3001a) cDNA libraries were plated at a density of $3 \times 10^4$ per 150 mm plate and replica lifted onto nylon filter circles. Cosmid and P1 inserts used in library screening were released from vector with Not I and purified from agarose gels. The cumulative length of inserts used as probe in a library screening was <80 kb to maintain adequate signal-to-noise. Insert DNA was labeled and pre-competed with 2 μg sCOS-1 vector in addition to $C_ot$-1 DNA. Positively hybridizing plaques were purified by standard techniques and insert DNA was excised (λZAPII) or subcloned (λgt10).

Identification of Mutations. The mutation in family 1605 was detected initially in RT-PCR template using the cDNA-based primers F11 (SEQ ID NO:8) (5'-GGGCTACCATAAAGCTTTG-3') and R11 (SEQ ID NO:9) (5'-GTTCATGTTCGATCAGTTCT-3') (205 bp product) and confirmed in genomic DNA using F11 with intronic primer IR11 (SEQ ID NO:10) (5'-GGGCTAGAAATACTCTTATCACC-3') (201 bp product). The mutations in families 97 and 1601 were initially detected in genomic DNA using intronic primers IF1C (SEQ ID NO:11) (5'-GCCTCAAGTGTTCCACTGAT-3') and IR1 (SEQ ID NO:12) (5'-AGGTTTTTCTGGGTAACCCTAG-3') (362 bp product). Amplifications were performed in standard conditions with hot start. Products were labeled by $\alpha^{32}$P-dCTP incorporation, diluted and denatured in formamide buffer prior to electrophoresis. SSCA was performed according to published protocols (Orita, M., et al. *Genomics* 5:874 (1989)). Sequencing of purified PCR products was performed with either an ABI 373a or 377 automated sequencing apparatus using cycle sequencing with dye terminator chemistries according to the manufacturer's protocol. The PCR primers were used as sequencing primers and all products were sequenced in both directions. The mutation in family 97 results in the loss of a Bsr I site. Genomic DNA amplified with IF1C and IR1 and digested with Bsr I yields products of 261 and 101 bp in the normal allele. The mutation in family 1605 results in the loss of a Taq I site. Genomic DNA amplified with F11 and IR11 and digested with Taq I yields products of 105 and 96 bp in the normal allele. The SSCA conditions used to demonstrate the mutation in the IF1C-IR1 genomic PCR product in family 1601 were 6% acrylamide (29:1), 1X TBE, on a 20 cm gel run at 14° C. and 100 V for 6 hours.

B. Discussion

The PKD2 genetic interval is flanked by the polymorphic markers D4S231 and D4S414/423 (Kimberling, W. J., et al. *Genomics* 18:467 (1993); Peters, D. J. M., et al. *Nature Genetics* 5:359 (1993)). A yeast artificial chromosome (YAC) contig and high density sequence tag site (STS) map of this region was constructed as described above (FIG. 1). Genetic studies in affected families using physically ordered polymorphic markers led to several progressive refinements of the PKD2 interval (Mochizuki, T., et al. *J. Am. Soc. Nephrol.* 5:631a (1994); San Millian, J. L., et al. *Am. J. Hum. Genet.* 56:248 (1995); Peters, D. J. M., et al. *Am. J. Hum. Genet.* 57:200a (1995); Constantinou-Deltas, C. D., et al. *Hum. Genet.* 95:416 (1995)). The closest unambiguous flanking genetic markers are AFMa059xc9 proximally and AICA1 distally (FIGS. 1A, B). A cosmid- and P1-based (Riess, O., et al. supra; Ioannou, P. A., et al., supra) contig extending over ~680 kb from AICA1 to the region centromeric to the polymorphic marker JSTG3 was constructed as described above (FIG. 1C). This contig contains a single gap of less than 40 kb. cDNAs corresponding to genes in this region were isolated using inserts from the genomic clones to screen either a human fetal brain or adult kidney cDNA library as described above. The mapping of the cDNA clones identified was confirmed and the clones were sequenced. These sequences were analyzed to identify open reading frames (ORF) and database searches using the BLAST algorithms (Altschul, S. F., et al. *J. Mol. Biol.* 215:403 (1990)) were performed.

One group of clones, collectively termed cTM-4, were initially isolated using insert DNA from cosmid c44a9 from the chromosome 4-specific cosmid library as described above (FIG. 1D). None of the cTM-4 clones have nucleotide level homology to any known genes, although 2 randomly-sequenced cDNA clones were identified (FIG. 1E). Northern blot hybridization with the cTM-4B3-3 insert (FIG. 1E) revealed a ~5.4 kb transcript expressed in most fetal and adult tissues (FIG. 2). cTM-4 is strongly expressed in ovary, fetal and adult kidney, testis, small and large intestine, and fetal lung. Peripheral blood leukocytes was the only tissue tested in which expression was not detected.

Initial database searching using the 6 translated reading frames obtained from the sequence of clone cTM-4B3-3 revealed amino acid level homology with polycystin, the PKD1 gene product (The European Polycystic Kidney Disease Consortium, *Cell*, 77:881 (1994); The International Polycystic Kidney Disease Consortium, *Cell* 81:289 (1995); The American PKD1 Consortium, *Hum. Mol. Genet.* 4:575 (1995); Hughes, J., et al. *Nature Genetics* 10:151 (1995)). Based on its map location, pattern of expression and the observed homology, the cTM-4 gene was further investigated as a candidate for PKD2. Nine overlapping cDNA clones were completely sequenced in both directions (FIG. 1E). The 5' end of the cTM-4 gene contains a pair of genomic Not I sites and the 3' end extends in the telomeric direction beyond the end of the P1 clone p157n2, into cosmid c44a9 (FIGS. 1C, 1D). The gene extends over 68 kb of the genome.

The consensus 5057 bp sequence (GenBank accession: gblU50928) is represented schematically in FIG. 1E. A translation start site with a good Kozak consensus sequence (5'-ACCGCG<u>ATG</u>G-3') (Kozak, M. *Nucleic Acids Res.* 15:8125 (1987)) was identified 67 bp from the 5' end of the K1-1 clone and 61 bases after an in-frame stop codon. It is followed by a 2904 bp ORF followed, in turn, by several in-frame stop codons. The 3' untranslated region is 2086 bp long and contains a consensus polyadenylation signal.

Figure 3:
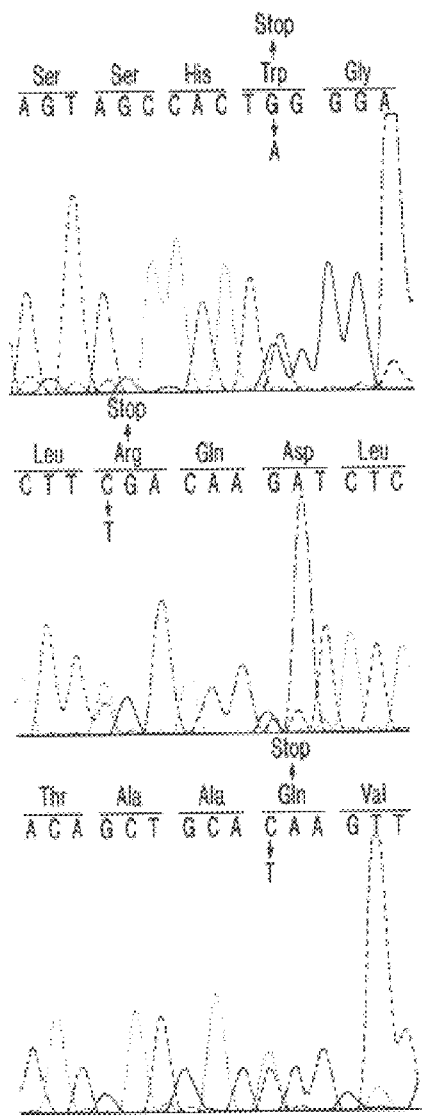
FIG. 3 depicts the mutations in PKD2 from an analysis of genomic PCR products in three PKD2 families. Left panel shows the results of direct sequencing of genomic PCR products from affected individuals. The arrows denote double peaks, confirmed by sequencing in both directions, indicative of heterozygosity at that nucleotide. Each of the mutant alleles results in a premature stop codon. The right panel demonstrates segregation of the mutated allele with the disease phenotype. In families 97 and 1605, the affected alleles are not digested by Bsr I and Taq I, respectively, since the restriction sites are lost by mutation. Family 1601 shows segregation of the SSCA variant, indicated by the arrow, with the disease phenotype. For each family, only portions of more extensive pedigrees are shown. Filled symbols, affected individuals. Open symbols, unaffected individuals. M, 100 bp ladder.
Figure 3:
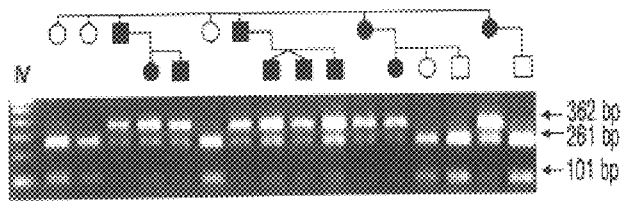
Figure 3:
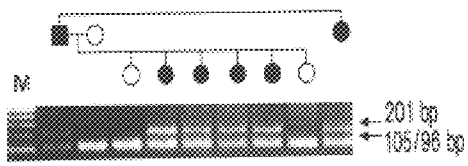
Figure 3:
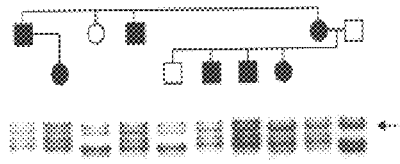

The DNA sequence and expression profiles of cTM-4 was next analyzed in unrelated affected individuals from families with PKD2 (Kimberling, W. J., et al. *N. Eng. J. Med.* 319:913 (1988); Kimberling, W. J., et al. *Genomics* 18:467 (1993); Peters, D. J. M., et al. *Nature Genetics* 5:359 (1993); Constantinou-Deltas, C. D., et al. *Hum. Genet.* 95:416 (1995)). Reverse transcribed RNA and genomic DNA templates were used to generate PCR products for, single strand conformational analysis (SSCA) as described above. Genomic PCR products of SSCA variants identified in three families were subjected to direct sequencing. Each affected individual was found to be heterozygous for a single base change that resulted in a nonsense mutation (FIG. 3). The mutation in family 97 is a G to A transition in the codon for Trp 380 (FIGS. 3, 4). The mutations in the Cypriot families 1605 and 1601 are C to T transitions in codons Arg 742 and Gln 405, respectively (FIGS. 3, 4). Using either the resultant loss of a restriction site in families 97 and 1605, or the SSCA pattern in family 1601, segregation of the mutation with the disease phenotype in each family was demonstrated (FIG. 3). Analysis of between 90 and 100 normal chromosomes failed to show the predicted affected allele in any case, making it less likely that these sequence differences represent anonymous polymorphisms. These limited findings do not provide evidence for clustering of mutations in PKD2.

The identification of mutations that disrupt the predicted translation product of cTM-4 and the segregation of these mutations with the ADPKD phenotype in three well characterized PKD2 pedigrees, provide strong evidence that cTM-4 is the PKD2 gene. The putative translation product of the cTM-4 ORF is a 968 amino acid sequence with a calculated molecular mass of 110 kD. Modeling with several hydrophobicity algorithms (Rost, B., et al. *Protein Sci.* 4:521 (1995); Klein, P., et al. *Biochim. Biophys. Acta* 815:468 (1985); Kyte, J. and R. F. Doolittle *J. Mol. Biol.* 157:105 (1982); Engelman, D. M., et al. *Annu. Rev. Biophys. Chem.* 15:321 (1986)) suggest that cTM-4 is an integral membrane protein with six (range, 5 to 8) membrane spanning domains and intracellular $NH_2$- and COOH-termini (Sipos, L. and G. von Heijne *Eur. J. Biochem.* 213:1333 (1993); Nakashima, H. and K. Nishikawa *FEBS Lett.* 303:141 (1992); Hartmann, E., et al. *Proc. Natl. Acad. Sci. USA* 86:5786 (1989)). Of the six highest scoring domains, the fourth transmembrane domain (tm4, FIG. 4), produced the lowest scores, but was consistently predicted to be a membrane span by several analyses (Rost, B., et al., supra; Klein, P., et al., supra; Kyte, J. and R. F. Doolittle, supra; Engelman, D. M., et al., supra). The "inside positive" rule (Sipos, L. and G. von Heijne, supra; Nakashima, H. and K. Nishikawa, supra; Hartmann, E., et al., supra) strongly supports the predicted topology. The majority of the N-glycosylation sites, occurring in the segment between tm1 and tm2 (FIG. 4), are predicted to be extracellular. In addition, potential phosphorylation sites were identified primarily in the COOH-terminal region, as was a putative EF-hand domain (Kretsinger, R. H. *Cold Spring Harb. Symp. on Quant. Biol.* 52:499 (1987); Babitch, J. *Nature* 346:321 (1990)), and this region is predicted to be intracellular (FIG. 4). If a stable protein product is produced, the mutations in families 97 and 1601 are expected to result in a product with an intact intracellular $NH_2$-terminal domain, first transmembrane domain, and part of the first extracellular loop. The mutation in family 1605 is predicted to result in a product lacking the portion of the intracellular COOH-terminus that contains several phosphorylation sites and the EF-hand domain (FIG. 4).

There is ~25% identity and ~50% similarity between the putative translation product of PKD2 and ~450 amino acids of polycystin and its *C. elegans* homolog, ZK945.9 (FIG. 4). There is a comparable degree of similarity with ~270 residues of the voltage activated $Ca^{2+}$ channel $\alpha_{1E}$ (VACCα1E-1; FIG. 4). The similarity between PKD2 and polycystin (and ZK945.9) extends over the region tm1 to tm6 in PKD2 but does not include the $NH_2$- and COOH-terminal domains. The corresponding region of polycystin has been predicted to contain four transmembrane segments (Hughes, J., et al. *Nature Genetics* 10:151 (1995)), three of these corresponding to tm1, tm2 and tm5 in the PKD2 gene product and the fourth localizing between tm5 and tm6 of PKD2. The regions corresponding to tm3 and tm4 of PKD2 were not predicted to be membrane spans in that report (Hughes, et al., supra).

The similarity to VACCα1E-1 (Williams, M. E., et al. *J. Biol. Chem.* 269:22347 (1994); Williams, M. E., et al. *Science* 257:389 (1992); Soong, T. W., et al. *Science* 260:1133 (1993); Horne, W. A., et al. *Proc. Natl. Acad. Sci. USA* 90:3787 (1993)) is presented as the strongest example of a general homology of PKD2 to the family of voltage activated $Ca^{2+}$ and $Na^+$ α1 channel proteins. These channel proteins contain four homologous domains (I–IV), each with six transmembrane spans (S1–S6), which are predicted to form the pore structure (Williams, M. E., et al. (1994), supra; Williams, M. E., et al. (1992), supra; Soong, T. W., et al., supra; Horne, W. A., et al., supra; Hille, B., *Ionic channels of excitable membranes* (Sinauer Associates, Sunderland, Mass., ed. 2, 1992), pp.250–7)). The membrane spans tm2 through tm6 as well as the intervening intracellular loops of PKD2 have similarity with corresponding segments in the α1 channels (FIG. 4). The similarity in the COOH-terminal region includes the putative EF-hand domain (FIG. 4) (Kretsinger, R. H., et al., supra; Babitch, J., supra). This domain in PKD2 scores highly on the EF-hand test (FIG. 4B) with identity at all the critical coordination vertices (Kretsinger, R. H., et al., supra; Babitch, J., supra). EF-hand domains are specialized helix-loop-helix motifs that have $Ca^{2+}$ binding activity in ~70% of proteins in which they occur (Nakayama, S. and R. H. Kretsinger *Annu. Rev. Biophys. Biomol. Struct.* 23:473 (1994)). Unpaired EF-hand sequences have recently been implicated in $Ca^{2+}$-sensitive inactivation of some forms of L-type VACCα1 (de Leon, M., et al. *Science* 270:1502 (1995)). EF-hand domains that do not coordinate $Ca^{2+}$ remain important to protein function (Kretsinger, R. H., et al., supra; Babitch, J., supra; Gulati, A., et al. *J. Biol. Chem.* 267:25073 (1992)).

Despite the observed homology to PKD1, the predicted structure of the PKD2 protein does not directly suggest a role in cell-cell or matrix-cell signaling similar to that proposed for polycystin (The European Polycystic Kidney Disease Consortium, supra; The International Polycystic Kidney Disease Consortium, supra.; The American PKD1 Consortium, supra; Hughes, J., supra). PKD2 does not have the large $NH_2$-terminal extracellular domain and the associated motifs found in polycystin (The European Polycystic Kidney Disease Consortium, supra; The International Polycystic Kidney Disease Consortium, supra; The American PKD1 Consortium, supra; Hughes, J., supra). It is possible that PKD2 functions in a parallel pathway with PKD1. However, given that the clinical diseases produced by mutations in PKD1 and PKD2 exhibit an identical spectrum of organ involvement, differing only in relative rates of progression of cystic changes, hypertension and the development of ESRD, the most likely scenario is that PKD2 associates with itself, with polycystin, and/or with other proteins and ligands as part of a common signal transduction pathway.

PKD2 bears some similarity to the α1 $Ca^{2+}$ (and $Na^+$) channels but has only six membrane spans. If it formed homo- or hetero-multimeric complexes (for example, with itself, with the homologous portion of PKD1 or with another protein), it could function as an ion channel or pore in a manner similar to the $K^+$ channels (Hille, B., supra). The observed homologies, the presence of a pair of conserved basic residues (Lys 573, Lys 576) in the fourth transmembrane domain, and the predicted even number of membrane spans, are consistent with such a role (Hille, B., supra). In such a model, PKD1 could act as the regulator of the PKD2 channel activity, perhaps with $Ca^{2+}$ as a second messenger in a signal transduction pathway. The discovery of PKD2 raises the possibility that the ADPKD phenotype may in part be the result of a defect in an unknown transport function.

All publications mentioned hereinabove are hereby incorporated by reference in their entirety.

While the foregoing invention has been described in detail for purposes of clarity and understanding, it will be appreciated by one skilled in the art from a reading of the disclosure that various changes in form and detail can be made without departing from the true scope of the invention in the appended claims.

What is claimed:

1. A method of detecting the presence of a mutation in the sequence of the PKD2 gene (SEQ ID NO:6) comprising the steps of:
   a) obtaining a polynucleotide sample from a subject;
   b) comparing the polynucleotide sample to a reference wild-type PKD2 sequence (SEQ ID NO:6); and
   c) determining the differences between the polynucleotide sample and the reference wild-type PKD2 sequence wherein the differences are mutations which comprise one or more deletion, insertion, point or rearrangement mutations.

2. The method of claim 1 wherein the subject is an embryo, fetus, newborn, infant or adult.

3. The method of claim 1, wherein the polynucleotide is DNA or RNA.

* * * * *